(12) United States Patent
Rokita et al.

(10) Patent No.: US 7,371,579 B1
(45) Date of Patent: May 13, 2008

(54) NICKEL-BASED REAGENTS FOR DETECTING DNA AND DNA-PROTEIN CONTACTS

(75) Inventors: Steven E. Rokita, Silver Spring, MD (US); Cynthia J. Burrows, Salt Lake City, UT (US)

(73) Assignee: The University of Maryland, College Park, MD (US)

( * ) Notice: Subject to any disclaimer, the term of this patent is extended or adjusted under 35 U.S.C. 154(b) by 975 days.

(21) Appl. No.: 10/019,655

(22) PCT Filed: Jul. 3, 2000

(86) PCT No.: PCT/US00/18325

§ 371 (c)(1),
(2), (4) Date: Aug. 6, 2002

(87) PCT Pub. No.: WO01/02370

PCT Pub. Date: Jan. 11, 2001

Related U.S. Application Data

(60) Provisional application No. 60/141,965, filed on Jul. 1, 1999.

(51) Int. Cl.
*C07D 235/02* (2006.01)
*C07F 15/04* (2006.01)
*C07K 2/00* (2006.01)
*G01N 33/52* (2006.01)
*G01N 33/58* (2006.01)
*G01N 33/60* (2006.01)
*G01N 33/68* (2006.01)
*C07K 14/795* (2006.01)

(52) U.S. Cl. .................. 436/86; 436/94; 530/300; 530/400; 534/10; 534/12; 536/25.4; 540/145

(58) Field of Classification Search ............... None
See application file for complete search history.

(56) References Cited

U.S. PATENT DOCUMENTS

| | | | |
|---|---|---|---|
| 5,258,492 A | 11/1993 | Schally et al. | |
| 5,268,371 A | 12/1993 | Mauclaire et al. | |
| 5,272,056 A | 12/1993 | Burrows et al. | |
| 5,595,726 A | 1/1997 | Magda et al. | |
| 6,004,530 A | 12/1999 | Sagner et al. | |
| 6,015,897 A * | 1/2000 | Theodore et al. | 540/474 |
| 6,087,493 A | 7/2000 | Wheelhouse et al. | |

FOREIGN PATENT DOCUMENTS

JP 3-38587 2/1991
WO WO 97/10854 A1 * 3/1997

OTHER PUBLICATIONS

Stemmler et al. The Sal-HX Motif for Metal-Mediated Oxidative DNA-Peptide Cross-Linking. Journal of the American Chemical Society. Jul. 9, 1999, vol. 121, No. 29, pp. 6956-6957.*
Routier et al. Highly Preferential Cleavage of Unpaired Guanines in DNA by A Functionalized Salen-Nickel Complex, Bioorganic & Medicinal Chemistry Letters. 1997, vol. 7 No. 1 p. 63-66.
Woodson, et al. A primer extension assay for modification of guanine by Ni(II) complexes. Nucleic Acid Research. 1993, vol. 21 No. 23 p. 5524-5525.
Brown, et al. Highly Specific Oxidative Cross-Linking of Proteins Mediated by a Nickel-Peptide Complex. Biochemistry 1995, 34, 4733-4739.
Shearer et al. Diamine Preparation for Synthesis of a Water Soluble Ni(II) Salen Complex. Bioorganic & Medicinal Chemistry Letters 9 (1999) 501-504.
Liang et al. Ni(II).Xaa-Xaa-His Induced DNA Cleavage: Deoxyribose Modification by a Common "Activated" Intermediate Derived from $KHSO_5$, MMPP, or $H_2O_2$, J. Am. Chem. Soc. 1998, 120, 248-257.

Routier, et al. Synthesis, DNA Binding, an Cleaving Properties of an Ellipticine-Salen-Copper Conjugate. Bioconjugate Chem. 1997, 8, 789-792.

Bhattacharya et al. Ambient Oxygen Activating Water Soluble Cobalt-Salen Complex for DNA Cleavage. J. Chem. Soc., Chem. Commun., 1995.

Tanaka et al. Synthesis of New Cationic Schiff Base Complexes of Copper(II) and Their Selective Binding with DNA. Bull. Chem. Soc. Jpn., 70, 615-629 (1997).

Gravert et al. Steric and Electronic Effects, Enantiospecificity, and Reactive Orientation in DNA Binding/Cleaving by Substituted Derivatives of [SalenMn$^{III}$]+ Inorg. Chem. 1996, 35, 4837-4847.

Gravert et al., Specific DNA Cleavage Mediated by [SalenMn(III)]+ J. Org. Chem. 1993, 58, 820-822.

Cheng et al. Novel Water-Soluble 4,4-Disubstituted Ruthenium(III)-Salen Complexes in DNA Stranded Scission. J. Chin. Chem. Soc. vol. 45, No. 5 1998.

Jacquet et al. Photoaddition of Ru(tap)$_2$(bpy)$^{2+}$ to DNA: A New Mode of Covalent Attachment of Metal Complexes to Duplex DNA. J. Am. Chem. Soc. 1997, 119, 11763-11768.

\* cited by examiner

*Primary Examiner*—Jeffrey Edwin Russel
(74) *Attorney, Agent, or Firm*—William E. Beaumont; Dickinson Wright, PLLC

(57) ABSTRACT

The invention relates to a compound comprising a labeled nickel complex (FIG. 1) that is used to detect and purify nucleic acid sequences by forming an adduct between a specific nucleic acid base and the labeled nickel complex. The adduct can also be purified through a separation process, such as affinity chromatography

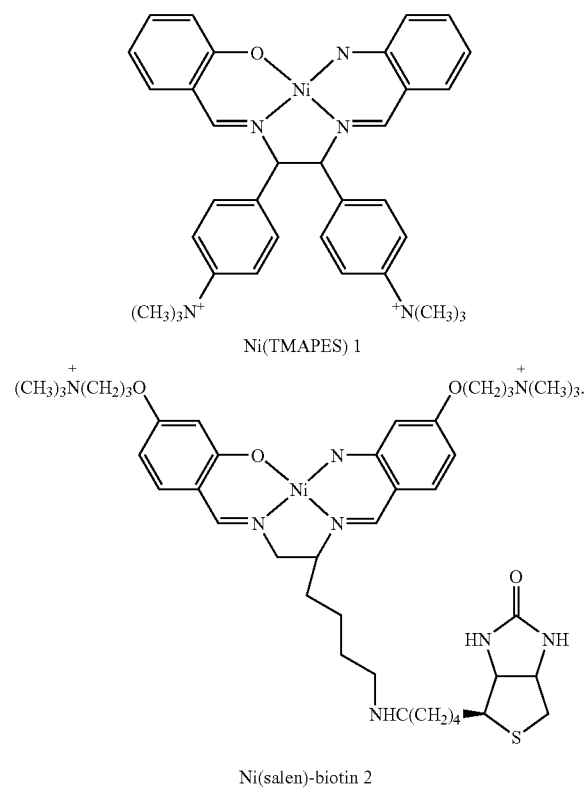

25 Claims, 6 Drawing Sheets

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaaatatcag atctaaaa                                                    18

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atatcagatc ta                                                          12

NICKEL-BASED REAGENTS FOR DETECTING DNA AND DNA-PROTEIN CONTACTS

CONTINUING DATA

This application claims the benefit of priority to U.S. Provisional Application No. 60/141,965, filed Jul. 1, 1999, the contents of which are incorporated herein by reference in their entirety.

GOVERNMENT INTEREST IN THE INVENTION

This invention was made with Government support under Grant Nos. GM-47531 and GM-49860 awarded by the National Institutes of Health. The Government has certain rights in this invention.

BACKGROUND OF THE INVENTION

The present invention relates to a nickel-based reagent that covalently binds to a specific nucleotide. The present invention also relates to a nickel-based salicylimine complexed to a histidine containing organic compound, as well as a nickel-based complex comprising a detectable label.

There are a variety of methods for detecting DNA/RNA-protein interactions and some depend on cross-linking. However, to the inventors' knowledge, there is no current technology that uses a nickel-based complex to covalently bind to a specific nucleotide and detect such binding and optionally isolating the DNA regions through use of a labeled complex.

A salicylimine containing nickel complex or any square planar, 4-coordinate nickel complex system linked with any detectable label is sufficient to practice the present invention. Moreover, the salicylimine containing nickel group complexed with the N-terminus of a polypeptide where the terminal amino acid is followed by a histidine or histidinyl residue results in a nickel based reagent that has additional desirable functional capabilities. If this terminal amino acid sequence is not naturally derived, then genetic manipulation may be used to append such a terminus on to any polypeptide of interest. For non-natural amino acids, chemical synthesis is preferred. Further, a semi-synthesis approach can be taken. Combining genetic and chemical means to obtain an amino acid sequence complexed with the salicylimine containing nickel complex is encompassed by the present invention. In addition, this complex may be used to add an aromatic aldehyde selectively to a nucleotide sequence which can be used as a handle for further modification or identification. Furthermore, whereas single-stranded regions of nucleic acids typically react more readily with various chemical and biochemical reagents, their detection and characterization method require prior knowledge of the target sequence. A nickel complex-identifier (such as biotin) of the invention will allow for purification and identification of the nucleic acid sequence without prior knowledge of the reactive sequence. Whereas there is no current reagent that selectively couples to and stays attached to the bound nucleotide, the nickel reagent of the invention allows for the detection of the bound sequence as well as isolation of the nucleotide region.

Shearer, J. M. and Rokita, S. E., Bioorg. Med. Chem. Lett. 9, 501-504, (1999), discloses the preparation of diamine compound for synthesis of a water-soluble Ni (II)-salen (salicylaldehyde) complex. This reference discloses a synthesis method for a simple, unconjugated Ni (Salen) called TMAPES. However, this reference does not disclose the attachment of a label or an adduct to this complex so that the complex can be detected biochemically.

Liang et al., J. Am. Chem. Soc., 120, 248-257 (1998), discloses a Ni (II) linked metallopeptide that is used to selectively degrade DNA through a minor groove binding interaction. However, this reference does not disclose or suggest the covalent linkage between a nickel containing complex and a specific nucleotide.

Routier et al., Bioconjugate Chem., 8, 789-792 (1997), discloses a conjugate between a salen and any biologically active molecule. The complex uses copper. However, such a copper conjugate cleaves nucleic acids non-specifically while non-covalently binding to the backbone of the nucleic acid. This is contrary to the present invention, which is directed to specific coupling of the nickel-containing complex to a nucleotide base.

Routier et al., Biooragnic & Medicinal Chemistry Letters, Vol. 7, No. 1, pp. 63-66 (1997), discloses a Ni-Salen complex. However, in this reference, coupling the Ni-Salen complex with the terminal N group would typically create a neutral compound that would be insoluble and not useful in coupling to nucleic acid bases.

Bhattacharya and Mandal, J. Chem. Soc., Chem. Common., 1995, pp. 2489-2490, discloses a Co-Salen chemistry. Again, this reference does not disclose formation of an adduct with nucleic acid.

Tanaka et al., Bull. Chem. Soc., Jpn. 70, 615-629 (1997), discloses the synthesis of a Cu-Salen molecule. This reference does not disclose or suggest formation of an adduct with nucleic acids.

Gravert and Griffin, J. Org. Chem., 58, 820-822 (1993), discloses a Mn-Salen complex. This reference does not disclose the formation of an adduct with nucleic acids.

Chen and Lu, Journal of the Chinese Chemical Society, 45, 611-617 (1998), discloses a Ru-Salen complex. This reference does not disclose or suggest the formation of an adduct with nucleic acids.

Jacquet et al., J. Am. Chem. Soc. 119, 11763-11768, (1997), discloses a Ru metal-Salen complex which requires photo-activation.

Gravert and Griffin, Inorg. Chem., 35, 4837-4847 (1996), discloses a Mn-Salen complex. However, this reference does not disclose the formation of an adduct with nucleic acids.

Brown et al., Biochemistry, 34, 4733-4739 (1995), discloses a nickel-His-tag and a nickel-glycylglycylhistidine for protein-protein cross-linking. However, the reference does not disclose nickel-dependent protein-nucleic acids or nucleic acid-biotin cross-linking.

U.S. Pat. Nos. 5,272,056 and 5,504,075 disclose a Ni(TMAPES) complex but fails to disclose attaching a detectable label to this complex. These two patents are incorporated herein by reference in their entirety.

As the literature described above shows, no salicylimine containing nickel complex is known in the prior art for the application of directly detecting or isolating nucleic acids. There is a need in the art for more effective method of studying chromosome structure, detecting specific nucleotide bases, and studying protein-DNA interactions.

The invention provides a salicylimine containing nickel complex for detecting protein-nucleic acid interactions and the presence of single-stranded regions of nucleic acids formed during gene expression, macromolecular assembly and chromatin reorganization.

SUMMARY OF THE INVENTION

The present invention has met all of the needs stated above.

Accordingly, there is provided a process for oxidatively modifying a nucleic acid comprising the steps of providing a nucleic acid containing a target nucleotide which includes guanine, and providing a nickel-reagent that has a square planar, 4-coordinate system linked to a detectable label, which is capable of oxidative covalent coupling to the nucleic acid at or near the target sequence in the presence of an oxidizing agent. Preferably, the nickel-reagent is a salicylimine containing nickel complex, or a nickel-porphyrin complex. The nucleic acid is contacted with the salicylimine containing metal complex in the presence of an oxidizing agent so that the nucleic acid is modified at or near the target nucleotide. This also allows for the isolation of the bound nucleotide sequence region.

Structures for the nickel complex are derivatives of Structures I-II:

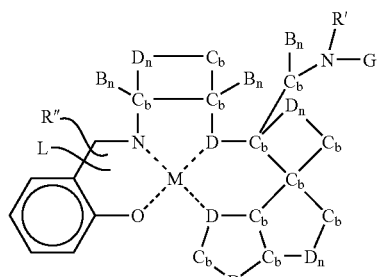

I

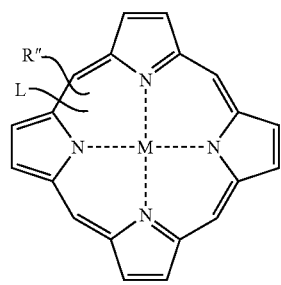

II wherein:
B independently represents doubly bonded oxygen;
C represents carbon;
D independently represents nitrogen, oxygen;
L is a detectable label, optionally attached to a linker;
M represents a nickel ion;
b=0-6;
n=0-1;
R independently represents a cationic group, optionally attached to a linker, wherein said cationic group is at least one $C_b$ group linked to a nitrogen atom, $(CH_2)_3NH_2$, $(CH_2)_4NH_2$, $C_bN(C_b)_{0-3}$,

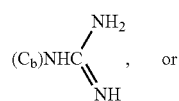, or pyridyl;

R' represents hydrogen, alkyl, aryl or a continued polypeptide chain;
R" is R or R' or G;
G represents OH, OR, a simple amide or a DNA delivery agent; and wherein all atoms contain sufficient bonds to adjacent atoms, to other atoms or to hydrogen to result in a stable structure, wherein, by independently representing is meant that within one structure, all values for the variables such as B, C, D, G, L, M, R, R', R", b, n, need not be the same, but may represent different atoms or numbers within a single structure.

The nickel complex of Structures I-II may be structures A-C or derivatives thereof:

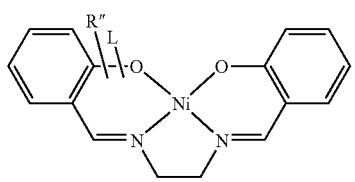

A

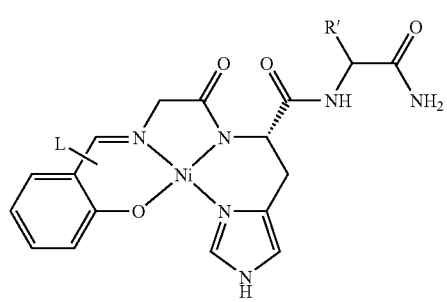

B

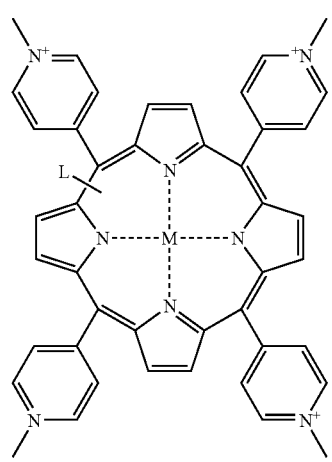

C

A kit is also provided for a nucleic acid assay for locating guanine groups in nucleic acids, oligonucleotides, polynucleotides, RNA and single-stranded DNA, and non-base paired guanine groups in double-stranded DNA. The kit comprises a labeled salicylimine containing metal complex selected from Structures I-II and their derivatives, an oxidant selected from the group consisting of peracid, sulfite and $O_2$, and optionally a base of piperidine, N-butylamine or sodium hydroxide when scission is desired.

Advantageously, the process of the invention provides a new method for detecting and isolating non-canonical DNA regions through guanine-specific modification of DNA.

Another object of the invention is to provide a nickel-based reagent to which is attached a detectable label so that the binding of the nickel-based reagent to a specific nucleotide base is detected by assaying for the label. The nucleic acid base is typically guanosine. A practical effect of the ability to detect the binding of the nickel-based reagent to the nucleic acid is the ability to isolate the bound DNA region.

It is another object of the present invention to provide a nickel-based reagent complex that is complexed with an amino acid sequence. Preferably, the amino acid sequence includes histidine. The label can be attached to either the Salen complex itself or to one of the amino acids. Preferably, Salen is complexed with an α-amino group on the N-terminal end of the amino acid sequence, and a histidine group, so that a square planar complex is formed with a nickel ion complexed with it.

Another object of the invention is to provide a reagent kit to serve industrial and academic research laboratories in research related to discerning the chromatin structure and protein-nucleic acid interaction.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein.

DETAILED DESCRIPTION OF THE INVENTION

Figure 1:
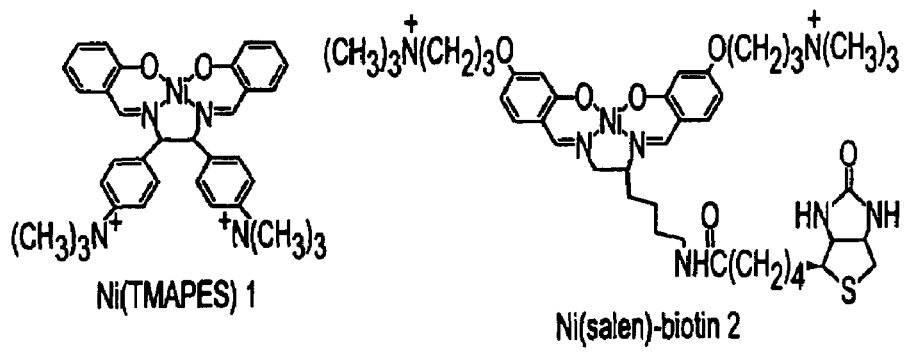
FIG. 1 shows Ni(salen) probes for nucleic acid structure.

The inventors have developed a series of labeled nickel-based complex that are square planar and 4-coordinate systems. Salicylimine containing nickel-based complexes to detect protein-DNA (RNA) interactions have been exemplified in the instant application. One of the advantages of the invention is that by using the complex of the present invention, regulatory regions of DNA can be identified and characterized. Furthermore, chromatin structure abnormalities can also be examined, and epigenetic modifications of chromosomes can be determined.

In a preferred embodiment, a model peptide-salicylaldimine complex was shown to exhibit the predicted ability to cross-link to DNA in the presence of nickel and an oxidant such as sulfite. This cross-link can either be maintained or further modified to leave only an aromatic aldehyde attached to the site of modification for additional conjugation to standard detection and purification appendages. This technology is now extended to full proteins and may also be elaborated for detection through standard protocols involving biotin, digoxigenin or a flag sequence recognition molecule, such as green fluorescent protein or a specific epitope. Furthermore, a related salicylaldimine complex has been linked to biotin for detecting single-stranded regions of DNA. This compound has been synthesized and has been tested with DNA.

It is to be understood that the invention is not limited to the particular nickel complex described above. At a minimum, the complex requires that at least the complex take a square planar, 4-coordinate system. Preferably, the complex may contain a salicylimine containing component, preferably salicylaldimine, and one or more additional component serving as a ligand to generate a square planar complex with nickel. In addition to the salicylimine containing group, the nickel complex may be complexed with porphyrin to provide a square-planar, 4-coordinate system. Additional components could be formed by linking other natural or nonnatural organic compounds such as amino acids to the complex. The complex should also be water-soluble, by for example, the presence of at least one positive charge on the complex in water. In addition, the complex can be conjugated to recognize elements to facilitate cellular or biomolecular localization in addition to purification and identification again through standard protocols involving biotin, flag sequence, antibodies and so on.

Abbreviations

| | |
|---|---|
| Rink Amide AM resin | 4-(2',4'-dimethoxyphenyl-Fmoc-aminomethyl-phenoxyacetamido-norleucylaminomethyl resin |
| Fmoc | Fluorenylmethoxycarbonyl |
| Pbf | 2,2,4,6,7-pentmethyldihydrobenzofuran-5-sulfonyl |
| Trt | trityl |
| Dde | 1-(4,4-dimethyl-2,6-dioxo-cyclohexylidene)ethyl |
| HBTU | 2-(1H-benzotriazole-1-yl)-1,1,3,3-tetramethyluronium hexafluorophosphate |
| DMF | dimethylformamide |
| TIS | triisopropylsilane |
| TFA | trifluoroacetic acid |

Abbreviations for amino acids used herein are conventionally defined as described hereinbelow unless otherwise indicated.

| Amino Acid | Three-letter abbreviation | One-letter symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Diaminopropionic acid | Dpr | |
| Glutamine | Gln | Q |
| Glutamine acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Ornithine | Orn | |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Unknown | Xaa | X |

Salicylimine Containing Compounds

The compounds useful in the invention are characterized in one regard by their ability to form stable complexes with transition metals. Stable complexes are those having measurable lifetimes at room temperature in water or common organic solvents.

The compounds comprise at least one ligand and a transition metal. A ligand is defined herein as a molecule that is attached to the central metal atom of a coordination compound. Preferred ligands are tetradentate or pentadentate and may comprise either macrocyclic or non-macrocyclic molecules. Other ligands, however, can also be used. It is to be understood that a tetradentate ligand has four donor atoms while a pentadentate ligand has five donor atoms.

The donor atoms may be nitrogen or oxygen. Preferably, at least two donor atoms are nitrogens, which are separated by from two to seven carbon atoms.

Suitable nitrogen donor groups are the amino group of peptides, or amines, imines, pyridines, imidazoles, pyrroles, and pyrazoles, with imine and pyridine groups preferred. The configuration may be square planar or pyramidal, with square planar preferred, but is not limited to these. Suitable oxygen donor groups are phenol, alcohol, carboxylic acid, and carbonyl. Examples of molecules containing oxygen donor groups are salens and salophens.

The ability of the ligands to form stable complexes results from the relative positions of the donor groups. Much of the rest of the ligand consists of carbon atoms that may be thought of as collectively forming a scaffold for maintaining the proper position of the donor groups.

Substituents on the atoms of the ligand affect the properties of the compounds, such as their ability to bind the nucleotides and DNA, their effectiveness in participating in the modification of nucleotides and DNA, their solubility in various solvents, and the stability of the complex they form with transition metals. The atoms of the ligands are normally substituted with sufficient hydrogen atoms to form a stable compound. It should be appreciated, however, that any positions in the ligands, whether or not so indicated herein, may be substituted with any other group and still do substantially the same thing in substantially the same way to accomplish the same result and are, therefore, to be considered equivalent to positions bearing hydrogen atoms as substituents for the purpose of determining the scope of the present invention.

Other suitable ligands are porphyrins such as structure C.

Some of the positions shown in Structures I-II and Structures A-C do not appear to be substitutents other than hydrogen. Nevertheless, these positions may be substituted by any organic or inorganic group without significantly affecting the ability of the compound to form a complex with transition metals.

Accordingly, any one or more of these positions may be substituted by an inorganic substituent, such as a doubly bonded oxygen, i.e., carbonyl, or a singly bonded oxygen i.e., hydroxy. Some additional inorganic groups include, for example, amino, thio, halo, i.e., F, Cl, Br, and I, etc.

Organic substituents include, for example, alkyl, aryl, alkylaryl and arylalkyl. The alkyl groups may be branched or unbranched and contain 20 carbon atoms or less, preferably 8 carbon atoms or less, and more preferably 4 carbon atoms or less. Some typical examples of alkyl groups include methyl, ethyl, n-propyl, isopropyl, n-butyl, sec-butyl, tert-butyl, isobutyl, and octyl. The alkyl groups may, in whole or in part, be in the form of rings such as cyclopentyl, cyclohexyl, cycloheptyl and cyclohexylmethyl. The cyclic groups described above may be further substituted with inorganic, alkyl, or aryl groups. Any of the alkyl groups described above may have one or more double or triple bond. Moreover, any of the carbon atoms of the alkyl groups may be separated from each other or from the ring nucleus with groups such as carbonyl, oxycarbonyl, oxy, amino, thio, etc. Alkyl groups may also terminate with groups such as halo, hydroxy, amino, carboxy, etc.

Aryl substituents are typically phenyl, but may also be any other aryl groups such as, for example, pyrrolyl, furanyl, pyridyl, thiazolyl, etc. The aryl groups may, further, be substituted by an inorganic, alkyl, or other aryl group. The alkylaryl and arylalkyl groups may be any combination of alkyl and aryl groups. These groups may be further substituted.

Particularly important substituent groups which may be present on the ligands are appended groups which are capable of binding to DNA or nucleotides. These will be called delivery agents. Suitable delivery agents may be of different types including intercalators, groove-binding agents, oligonucleotides, proteins or protein fragments, and polyamines. The intercalators include ethidium, methidium, acridine, proflavin, phenanthroline, etc. The groove-binding agents include distamycin and netropsin. A distamycin derivative was used to direct nucleotide scission by Schultz, P. G., et al., "Design and Synthesis of a Sequence-Specific DNA Cleaving Molecule. (Distamycin-EDTA) iron(II)", J. Am. Chem. Soc. 104, 6861-6863 (1982). Oligonucleotides may bind producing double helical or triple helical areas. Proteins or protein fragments which bind DNA include Hin recombinase (Mack, D. P. and Dervan, P. B., "Nickel-Mediated Sequence-Specific Oxidative Cleavage of DNA by a Designed Metalloprotein", J. Am. Chem. Soc. 112, 4604-4606 (1990)). The useful polyamines include spermine and spermidine described by K. D. Stewart, "The Effect of Structural Changes in a Polyamine Backbone on its DNA-Binding Properties", Biochem, Biophys. Res. Comm. 152, 1441-1446 (1998).

The Labeled Complexes

Ligands to be used in the invention form stable complexes with transition metal ions. For the purpose of this specification, transition metals are to be understood as including metals having partly filled d or f shells in any of their commonly occurring oxidation states. The useful transition metals include ions of Ni, Co, Cu, Rh, Pd, Ir, Pt, Cr, Mn, Fe, Ru, and Os. Preferred are ions of Ni, Co and Pd. Most preferred is Ni.

The complexes are formed by contacting a salt of the metal ion with the ligand in a suitable solvent, for example, water and methanol. Progress of the complexation is easily followed visually or spectrophotometrically. Depending upon reaction conditions such as the ligand, the metal, the pH, and the solvent, the complexation reaction may occur rapidly at room temperature, or may require heating.

The complexes may be four, five or six coordinate with four preferred and square planar most preferred.

The complexes may be deprotonated, but an overall positive charge is preferred, and a highly positive charge is most preferred. Balancing anions, counterions, or salts may be as known to those skilled in the art, such as derivatives of salts e.g. perchlorate, acetate, nitrate, chlorides, bromides, iodides, and tetrachlorozincate ($ZnCl_4^{-2}$).

The ligand-metal complexes are used in the process of the invention to modify oligonucleotides, single-stranded DNA, non-classical duplex structures and double-stranded DNA having particular conformations, that is, extra-helical areas, cruciform DNA, abasic (non base paired G's) areas, unpaired ends, and telomeres (ends of chromosomes). In double stranded DNA, the modification is specific to these conformational areas. The oligonucleotides may be naturally occurring or synthetic. The single-stranded DNA may also be derived from separation of duplex DNA. All forms of RNA are targets for reaction also.

A non-diffusible species is important for site-specificity in the target nucleotide. In contrast, certain complexes, e.g. Fe(II)-EDTA plus ligand, generate hydroxyl radicals which react with DNA non-specifically. In this type of non-preferred complex, the complex attaches to a binding site and generates a reactive species which diffuses with a loss of specificity. In the system described herein, the metal complex binds to a particular DNA site and the reactive agent is produced at that site when oxidant is present. A non-diffusible species is one which reacts with DNA before it is released from the specific binding site.

The complexes are used to modify or optionally nick DNA or nucleotides when used with an oxidant. Some examples of oxidizing agents include peracids such as peroxymonosulfate salts, e.g. potassium peroxymonosulfate ($KHSO_5$) which is commercially available under the trademark OXONE, magnesium monoperoxyphthalate (MMPP), and oxygen in combination with sulfite. Particularly preferred are MMPP or $O_2$ and sulfite. In physiological systems, a combination of oxygen and sulfite is preferred.

After oxidation, excess oxidant may be quenched with a high concentration of reductant such as sodium sulfite, and base treatment may be used for cleavage. Other quenching agents may include 10 mM EDTA or β-mercaptoethanol. Optionally, if scission of nucleic acid is desired, suitable bases are piperidine, N-butylamine and sodium hydroxide with a pH of about 9-13.

Reaction conditions include a temperature from about zero to about 100° C., from about 20° C. to about 40° C. preferred and 25°-37° C. most preferred. Reaction time is at least about 30 seconds, from about 10 minutes to an hour preferred and from about 15 minutes to about 30 minutes most preferred. The reaction may be left for an extended period of time, e.g. up to 48 hours without adverse effects. The pH may be about 3-10, with 6.5-7.5 preferred.

For a reaction involving, for example, a nucleotide concentration of about 0.1 to about 50 picomoles of labelled 5'-ends, the metal complex may be used in an amount of from about 0.1 µM to about 10 mM, with from about 0.5 µM to about 100 µM preferred and from about 1 µM to about 10 µM most preferred. The oxidant may be used in an amount of from about 0.1 µM to about 10 mM with about 50 µM to about 100 µM preferred. The ratio of metal complex to oxidant may range from about 99:1 to about 1:99. The oxidant is preferably in excess of the metal complex with a ratio of metal complex:oxidant ranging up to about 1:10, 000, with from about 1:1 to about 1:50 preferred and 1:1 to 1:2 most preferred.

In vitro, the nucleotide or DNA is labelled in any suitable manner such as with radiolabel, and standard electrophoresis and autoradiography may be used to determine the level of modification.

The process of the invention for modifying DNA or sequencing is suitable for being attained using a kit. The kit may comprise a salicylimine containing metal complex to be used with an oxidant and optionally a base. The kit can supply a salicylimine containing metal complex in an amount of from about 0.01 to about 500 µM metal complex, preferably from about 0.1 to about 50 µM metal complex and most preferably about 10 to about 50 µM metal complex. An oxidant is selected from the group consisting of peracid, sulfite and $O_2$. The preferred oxidants are oxone, MMPP, or a combination of sulfite and oxygen. The most preferred oxidant is MMPP. If the kit is to be used in an in vivo system, e.g., in tissue culture or in an animal, the oxidant is preferably provided by dissolved oxygen already present in the system, with the addition of sulfite. A base may also be provided, optionally and may be piperidine, N-butylamine or sodium hydroxide having a pH of about 9-13, if scission of the DNA is desired.

As used herein, "label" or "detectable label" refers to any molecule that is linked to the Ni-salen complex to provide a detectable signal. The label may be radioactive, chemiluminescent, a protein ligand, or an enzyme, or if a fluorescent group is used, a different fluorescent group may be used for different types of salicylimine containing nickel complexes. These fluorescent tags would have the property of having spectroscopically distinguishable emission spectra. If a protein ligand based detection method is desired, biotin or digoxigenin are examples of compounds that may be used as a detectable label. In the case of digoxigenin, enzymes linked to anti-digoxigenin antibodies may be used to detect the presence of digoxigenin. Enzyme-based detection assays include for example, the use of peroxides and alkaline phosphatase, to obtain chromogenic substances. ELISA assays can be typically used in the practice of the instant invention.

However, it should be appreciated that the choice of a label depends merely on the preference of the person of ordinary skill in the art as the present invention can be performed with any detectable label at all.

The label can be linked anywhere on the salicylimine containing nickel complex. The label is preferably linked on the carbon backbone. More preferably, the label is linked adjacent to the salicylimine group. It should be understood that binding of the label to the complex can occur practically anywhere on the carbon backbone or a substituent of the backbone, directly or through a linker, such that a person of skill in the art would be able to attach the label to the nickel complex. Any group having a primary amine group could be a site of binding of the label. The person of skill in the art would known to attach a label to the nickel complex so that the label does not interfere with the binding of the salen group to the nucleic acid. For example, the attachment of the label should not destroy or hinder the formation of a square planar, 4-coordinate system.

As used herein, "linker" means any organic residue that serves to link the label to the nickel complex. Such a linker may be, without limitation, an alkyl group, or a compound having multiple $CH_2$ groups, an aryl group, an arylalkyl group, ethers, and so on. Other variations and substituents are possible, so long as the linker serves to connect the label to the nickel complex without hindering the binding of the complex to the nucleic acid.

Another object of the invention is to provide a method of purifying the nickel-complex-nucleotide adduct (covalently bound). If a biotin label is linked to the nickel complex, for example, then an avidin column may be used to bind the biotin label, and thereby purify the entire adduct, including the nucleic acid region. If another protein ligand is used as the label, then using a separation process comprising its corresponding antibody may be similarly used in an affinity chromatography procedure, for example. Other methods can be used so long as the method takes advantage of the covalent binding between the nickel-complex with a specific nucleotide, and that the nickel complex is directly or indirectly attached to a detectable label.

In another aspect of the invention, a library of metals, salicylaldehydes, oxidants and peptides may be screened to determine the best candidates for oxidative cross-linking to DNA. The salicylaldehyde-guanine adducts that have already been observed may be the subject of further mechanistic studies, with a view toward providing information relevant to tyrosine-DNA cross-linked lesions.

Another feature of the invention is that the Salen-LysHis metal-binding motif may be appended to the N terminus of peptide nucleic acids (PNA) for targeting specific sites in DNA or RNA oligonucleotide targets. Base specificity is examined, and the structures of potential C, T, and A adducts are determined using ESI-MS/MS from both oligomer and nucleoside model studies. Salicylaldehyde adducts may be further functionalized with biotin and fluorescein reagents or any other label.

With the Ni(Salen-LysHis) complex in hand as a redox active complex for oxidative coupling to DNA bases, we next sought the ideal recognition agent, or delivery vehicle, to target specific sites in nucleic acids. peptide nucleic acid (PNA) oligomers have outstanding properties for nucleic acid binding and ease of synthesis. PNA now enjoys widespread use in biological chemistry since its initial discovery in 1991. Its applications range from genome cutting to drug delivery to in situ hybridization. Some of the pertinent features of PNA, include:

- PNAs obey Watson-Crick rules for base pairing and form a regular "antiparallel" duplex helical structure with DNA in that the N terminus of PNA normally binds with the 3' end of a DNA oligo. Parallel duplexes are also possible, but less stable. Crystal structures show conformations similar to B-form DNA for PNA-DNA. PNA-RNA has been analyzed by NMR spectroscopy and indicates an A-like helix for the RNA.
- PNAs have high binding affinity for DNA because of their neutral charge. A PNA-DNA duplex shows a melting temperature typically 1° C. higher per base pair than a DNA-DNA duplex. The stability of PNA-RNA duplexes is even higher—about 1.5° C. per base pair higher than RNA-RNA duplexes.
- A consequence of the higher $T_m$'s is that shorter sequences may be used to impart high stability to a duplex. Furthermore, a PNA oligomer will displace a DNA strand from a duplex in order to bind to its target DNA.
- PNA is less forgiving of base pair mismatches than is DNA. A single mismatch typically leads to an 8-20° C. lowering of the $T_m$ in a PNA-DNA duplex. This means that high sequence selectivity is ensured.
- PNA forms triple helical structures but these are primarily restricted to polypyrimidine sequences. $(PNA)_2$-DNA is more stable than PNA-$(DNA)_2$.
- PNA is readily synthesized using either fmoc or Boc methodology on solid support; both types of the 4 protected base monomers are commercially available. The methodology is completely compatible with peptide synthesis and several peptide-PNA conjugates are known.
- PNA shows high chemical stability to HF, ammonia and piperidine and remarkably high biostability in both human serum and cell extracts.
- The cellular uptake of PNAs is low although DNA/PNA chimeras are taken up by Vero cells and NIH3T3 cells at low (1 μM) extracellular concentration.
- Applications of PNA currently include diagnostic methods for screening for genetic mutations, probes in pre-gel hybridization techniques (an alternative to Southern blotting) and agents for assisting MALDI-TOF analysis of single-nucleotide polymorphisms in the human genome.

The following examples are offered by way of illustration of the present invention, and not by way of limitation.

EXAMPLES

Example 1

Synthesis and Activity of Ni(II)-Salen-Biotin Complex 2

The oxidation and coordination chemistry of transition metal ions offer substantial opportunities for selective recognition and modification of nucleic acids. (Sigel, H., Sigel, A. Eds.; Marcel Dekker: *Metal Ions in Biological Systems*, Vols. 32 and 33; Dekker: New York, 1996.) (Pyle, A. M; Barton, J. K. *Prog. Inorg. Chem.* 1990, 38, 413-475.) Certain nickel complexes in particular have demonstrated alternative abilities to oxidize and couple with highly accessible guanine residues in the presence of $O_2$ and sulfite (Muller, J. G.; Hickerson, R. P.; Perez, R. J.; Burrows, C. J. *J. Am. Chem. Soc.* 1997, 119, 1501-1506.) (Stemmler, A. J.; Burrows, C. J. *J. Am. Chem. Soc.* 1999, 121, 6956-6957.) or peracids such as monoperoxysulfate or monoperoxyphthalate. (Burrows, C. J.; Rokita, S. E. *Acc. Chem. Res.* 1994, 27, 295-301.) (Burrows, C. J.; Rokita, S. E. In *Metal Ions in Biological Systems*, Vol. 32; Sigel, H., Sigal, A. Eds. Dekker: New York, 1996; Chapter 18, pp. 537-560.) (Rokita, S. E.; Burrows, C. J. in *Current Protocols in Nucleic Acid Chemistry;* Beaucage, S. I., Bergstrom, D. E., Glick, G., Jones, R. A. Eds. Wiley, New York, 2000; Chapter 6.4.) (Muller, J. G.; Paikoff, S. J.; Rokita, S. E.; Burrows, C. J. *J. Inorg. Biochem.* 1994, 54, 199-206.) (Muller, J. G.; Kayser, L. A.; Paikoff, S. J.; Duarte, V.; Tang, N.; Perez, R. J.; Rokita, S. E.; Burrows, C. J. *Coord. Chem. Rev.* 1999, 185-186, 761-774.) Adducts formed between guanine and nickel complexes based on the salen ligand (ethylene-N-N'-bis(salicyaldimine)) strongly inhibit polynucleotide elongation catalyzed by reverse transcriptase and DNA polymerase and consequently allow for sensitive detection through primer extension assays. (Muller, J. G.; Paikoff, S. J.; Rokita, S. E.; Burrows, C. J. *J. Inorg. Biochem.* 1994, 54, 199-206.) (Muller, J. G.; Kayser, L. A.; Paikoff, S. J.; Duarte, V.; Tang, N.; Perez, R. J.; Rokita, S. E.; Burrows, C. J. *Coord. Chem. Rev.* 1999, 185-186, 761-774.) (Woodson, S. A.; Muller, J. G.; Burrows, C. J.; Rokita, S. E. *Nucleic Acids Res.* 1993, 21, 5524-5526. Pan, J.; Woodson, S. A. *J. Mol. Biol.* 1998, 280, 597-609.)

The salen ligand serves two functions by activating the redox chemistry of the bound Ni(II) and generating a ligand-centered radical for addition to guanine. (Muller, J. G.; Paikoff, S. J.; Rokita, S. E.; Burrows, C. J. *J. Inorg. Biochem.* 1994, 54, 199-206.) (Muller, J. G.; Kayser, L. A.; Paikoff, S. J.; Duarte, V.; Tang, N.; Perez, R. J.; Rokita, S. E.; Burrows, C. J. *Coord. Chem. Rev.* 1999, 185-186, 761-774.) (Goldsby, K. A., *J. Coord. Chem.* 1988, 19, 83-90.) (Goldsby, K. A.; Blaho, J. K.; Hoferkamp, L. A. *Polyhedron* 1989, 8, 113-115.) Direct coordination between a transient Ni(III) intermediate and accessible N7 sites on guanine appear to enhance the specificity. (Shih, H. -C.; Kassahun, H.; Burrows, C. J.; Rokita, S. E. *Biochemistry* 1999, 38, 15034-15042) Previous investigations have focused on the water-soluble salen complex 1, NiTMAPES (FIG. 1), but a wide range of useful derivatives can be envisioned including a salen-peptide hybrid (Stemmler, A. J.; Burrows, C. J. *J. Am. Chem. Soc.* 1999, 121, 6956-6957.) (Muller, J. G.; Paikoff, S. J.; Rokita, S. E.; Burrows, C. J. *J. Inorg. Biochem.* 1994, 54, 199-206.) (Muller, J. G.; Kayser, L. A.; Paikoff, S. J.; Duarte, V.; Tang, N.; Perez, R. J.; Rokita, S. E.; Burrows, C. J. *Coord. Chem. Rev.* 1999, 185-186, 761-774) (Shearer, J. M.; Rokita, S. E. *Bioorg. Med. Chem. Lett.* 1999, 9, 510-504.) These nickel salens appear unique in their ability to couple with their targets rather than promote direct strand scission as common to the salen complexes of Mn, Co and Cu. (Muller, J. G.; Kayser, L. A.; Paikoff, S. J.; Duarte, V.; Tang, N.; Perez, R. J.; Rokita, S. E.; Burrows, C. J. *Coord. Chem. Rev.* 1999, 185-186, 761-774.)

Although footprinting well-defined polynucleotides with NiTMAPES may be routine with piperidine cleavage or primer extension, obtaining the actual products of coupling can be an arduous task. As the heterogeniety of the system increases, even footprinting becomes difficult. This type of problem is common in molecular biology, and its solution often relies on a broad range of techniques based on biotin. Labeling, detecting and purifying any biotinylated species regardless of its complexity is made possible by the extraordinary affinity of biotin for avidin and streptavidin. (Launer, H. F.; Fraenkel-Conrat, H. *J. Biol. Chem.* 1951, 193, 125-132.) (Green, N. M. *Biochem. J.* 1963, 89, 585-620. Green, N. M. *Adv. Protein Chem.* 1975, 29, 85-133.) (Diamonds, E. P.; Christopoulos, T. K. *Clin. Chem.* 1991, 37, 625-636.) (Wilchek, M.; Edward, E. A., Eds. *Methods in Enzymol.* 1990, 184, entire volume.) The properties of a combined Ni(salen)-biotin conjugate should then have the potential to diagnosis and isolate genomic sequences containing noncanonical structures of guanine. The first synthesis of such a conjugate and its initial characterization with a model oligonucleotide is described herein.

Early synthetic targets were designed in direct analogy to TMAPES and were expected to support a range of strategies for biotinylation. However, the instability and low reactivity of the essential intermediates precluded this scheme. These problems were avoided in a subsequent approach that relied on a triamine first developed by the laboratory of Bailly for use in construction of Cu(salen) derivatives. (Routier, S.; Bernier, J -L.; Waring, M. J.; Colson, P.; Houssier, C.; Bailly, C. *J. Org. Chem.* 1996, 61, 2326-2331.) (Routier, S.; Cotelle, N.; Catteau, J. -P.; Bernier, J. -L.; Waring, M. J.; Riou, J. -F.; Bailly, C. *Bioorg. Med. Chem.* 1996, 4, 1185-1196.) $N_\alpha$—Z—$N_\epsilon$-BOC-L-lysine 3 was converted to its nitrile derivative 4 as described previously (FIG. 2). (Routier, S.; Bernier, J -L.; Waring, M. J.; Colson, P.; Houssier, C.; Bailly, C. *J. Org. Chem.* 1996, 61, 2326-2331.) (Routier, S.; Cotelle, N.; Catteau, J. -P.; Bernier, J. -L.; Waring, M. J.; Riou, J. -F.; Bailly, C. *Bioorg. Med. Chem.* 1996, 4, 1185-1196.) A subsequent procedure requiring hydrogenation under high pressure was avoided by use of two sequential hydrogenations in the presence of Raney nickel and then Pd/C to yield the diamine 5 (see Example 2 for experimental details). The BOC-protected salen derivative 6 was formed by condensation of this diamine under $N_2$ with two equivalents of 2,4-dihydroxybenzaldehyde in the presence of $Ni(OAc)_2$. Deprotection by standard conditions (dry $TFA/CH_2Cl_2$) and coupling with the commercially available N-hydroxysuccinimide ester of biotin (BNHS) produced the neutral and water-insoluble derivative 7. The obligatory solubility in water was achieved through alkylation of the two free phenolic oxygens with 3-bromopropyltrimethyl ammonium bromide. (Kayser, L. A., M. S. thesis, University of Utah, 1997.) The desired perchlorate salt of 2 was precipitated by addition of $KClO_4$ and recrystallized from $MeOH/Et_2O$.

Data from electrospray mass spectroscopy as well as $^1$H- and $^{13}$C-NMR were consistent with the desired product.

Figure 3:
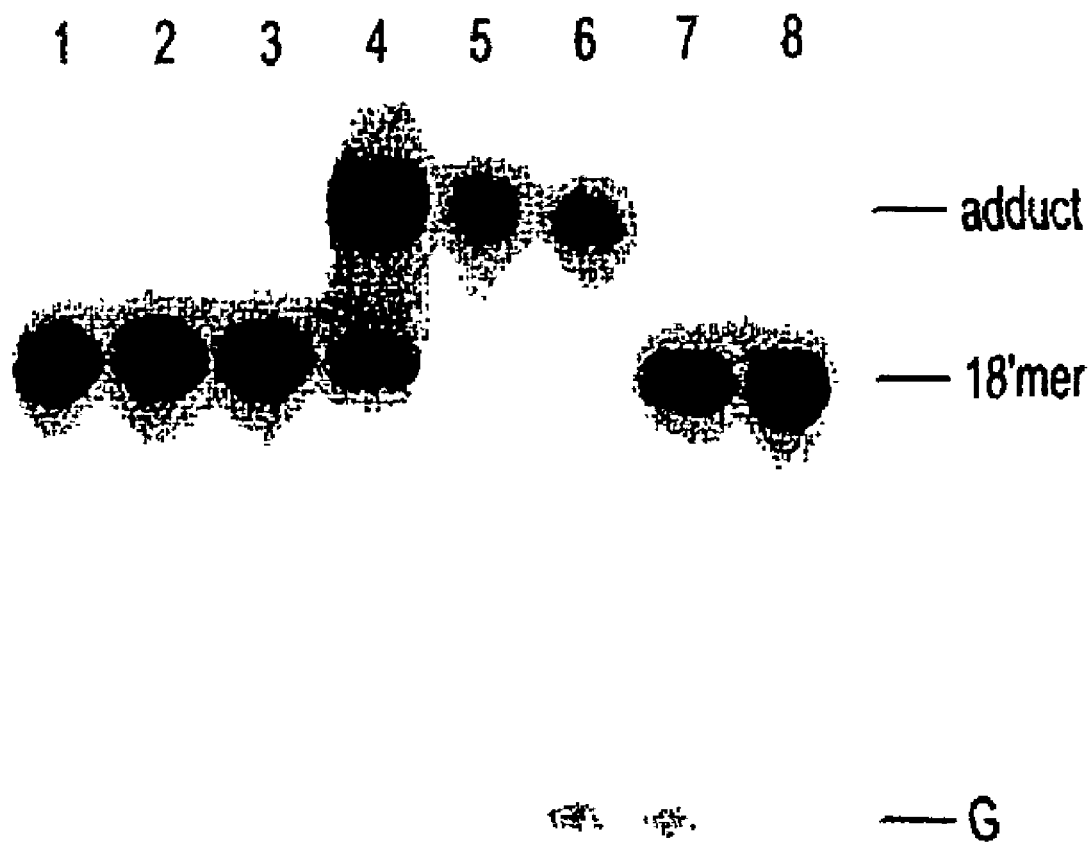
FIG. 3 shows a phosphorimage of a denaturing polyacrylamide gel (20%, 7 M urea) used to identify the high-molecular weight conjugate formed between DNA and Ni(salen)-biotin. The 5'[$^{32}$P] labeled oligodeoxynucleotide (18' mer), 5'-d(AAAATATCAGATCTAAAA; SEQ ID NO: 1) (12 mM, 6 nCi), in 10 mM sodium phosphate pH 7 (lane 1) was alternatively incubated with Ni(salen)-biotin 2 (50 mM, lane 2), MMPP (120 mM, lane 3) and their combination (lane 4). The resulting DNA conjugate was isolated from a monomeric avidin affinity column (lane 5) and subsequently treated with piperidine (0.2 M, 90° C., 30 min, lane 6). A standard G-lane was generated by dimethylsulfate as described by Maxam and Gilbert (lane 7) (Maxam, A. M.; Gilbert, W. *Methods Enzymol.* 1980, 65, 499-560). As a control, the parent oligonucleotide was also treated with piperidine (0.2 M, 90° C., 30 min, lane 8).

Incubation of a model oligonucleotide (18' mer, one central G) with the Ni(salen)-biotin conjugate 2 (50 μM) or the magnesium salt of monoperoxyphthalic acid (MMPP) (120 μM) in 10 mM sodium phosphate pH 7 generated no apparent products as detected by denaturing polyacrylamide gel electrophoresis (FIG. 3, lanes 2 and 3). However, their combined presence produced a high molecular weight DNA adduct in approximately 60% yield (FIG. 3, lane 4). This yield decreased to 5% when the ionic strength of the mixture was increased by addition of 100 mM NaCl. In either case, reaction remained specific for the sole guanine residue as indicated below. The biotinylated DNA was conveniently separated from its parent oligonucleotide with a monomeric avidin matrix (Pierce) and desalted with reverse-phase (C-18) chromatography (FIG. 3, lane 5). Subsequent treatment with hot piperidine was investigated since this condition had previously induced a diagnostic strand scission of adducts formed by NiTMAPES 1. (Muller, J. G.; Paikoff, S. J.; Rokita, S. E.; Burrows, C. J. *J. Inorg. Biochem.* 1994, 54, 199-206.) (Muller, J. G.; Kayser, L. A.; Paikoff, S. J.; Duarte, V.; Tang, N.; Perez, R. J.; Rokita, S. E.; Burrows, C. J. *Coord. Chem. Rev.* 1999, 185-186, 761-774.) The adduct of conjugate 2 demonstrated equivalent lability in the presence of hot piperidine. The resulting oligonucleotide fragment co-migrated with the guanine standard produced by Maxam-Gilbert sequencing (FIG. 3, lanes 6 and 7, respectively). (Maxam, A. M.; Gilbert, W. *Methods Enzymol.* 1980. 65, 499-560.) As expected, the parent oligonucleotide exhibited no sensitivity to piperidine (FIG. 3, lane 8).

Composition of the isolated adduct was confirmed by mass spectral analysis. Electrospray mass spectroscopy identified a major species of mass 6377 that is consistent with the oligonucleotide+Ni(salen)+oxygen. The additional oxygen was anticipated from MMPP-dependent oxidation of the biotin sulfide. Incubation of the unconjugated biotin under conditions analogous to the DNA experiments above led to formation of biotin sulfoxide as indicated by comparison to a standard produced by known reaction with $H_2O_2$. (Melville, D. B. *J. Biol. Chem.* 1954, 208, 495-500.) This oxidation did not significantly interfere with avidin affinity chromatography since the major determinant for recognition is the ureido group of biotin. (Weber, P. C.; Ohlendorf, D. H.; Wendoloski, J. J.; Salemme, F. R. *Science* 1989, 243, 85-88.)

The ability of the nickel complex to deliver a biotin tag to accessible guanine residues allows for the isolation and characterization of noncanonical structures in complex systems such as chromatin. Few alternatives are currently available that share both a dependable conformational specificity and an easy assimilation into the wide ranging and powerful techniques based on biotin recognition.

Example 2

Figure 2:
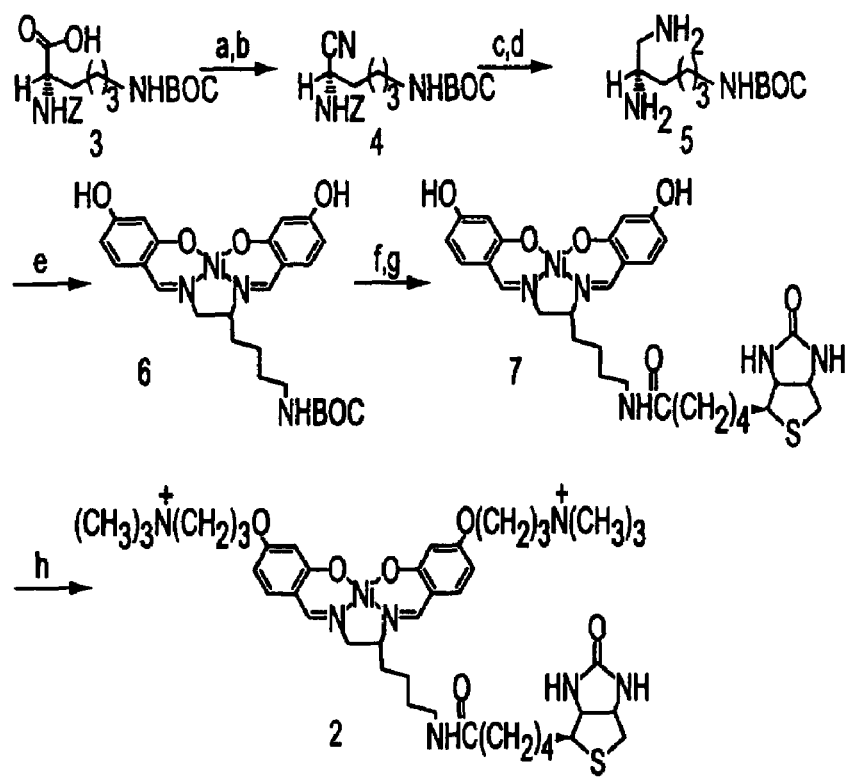
FIG. 2 shows synthesis of a Ni(salen)-biotin conjugate with solubility in water. Reagents and conditions (a), $Et_3N$, ClCOOEt, $NH_3$, THF, 10° C.-rt, 56%. (b) $(CF_3CO)_2O$, $Et_3N$, THF, $N_2$, 0° C., 87%. (c) $H_2$, Ra—Ni, 6.8 atm, $NH_3$, MeOH, 3 days, 72%. (d) $H_2$, Pd/C, MeOH, rt, overnight, 82%. (e) 2, 4-dihydroxy-benzaldehyde, $NiAc_2$, EtOH, reflux, $N_2$, 3 hr, 78%. (f) TFA, $CH_2Cl_2$, rt, 0.5 h, 86%. (g) BNHS, $Et_3N$, DMF, 4° C., 3 days, 22%. (h) $Br(CH_2)_3N(CH_3)_3Br$, DMF, rt, 3 days, 80%.

Materials and Methods used in the Synthesis of Ni(Salen)-Biotin Conjugates 2 Depicted in FIG. 2

General. $^1$H and $^{13}$C NMR spectra were recorded on Bruker DPX 400 and 500 spectrometers. Chemical shifts are reported as δ values relative to internal standards such as $CHCl_3$, $CH_3OH$ or $CH_3CN$. Mass spectra were determined using VG 7070E (FAB) and Micromass Quattro II triple quadrupole (electrospray) instruments. Column chromatography was performed with Merck kieselgel 60 silica (230 ASTM). $CH_2Cl_2$ was distilled from calcium hydride; EtOH was distilled from Mg; DMF was distilled from $MgSO_4$; and TFA was distilled from $P_2O_5$. Other solvents and chemicals were used as received.

(S)-N'-(Benzyloxycarbonyl)-1,5-diaminopentane. (S)-1-Cyano-N1-(benzyloxycarbonyl)-N5-(tert-butyloxycarbonyl)-1,5-diaminopentane (Routier, S.; Bernier, J -L.; Waring, M. J.; Colson, P.; Houssier, C.; Bailly, C. *J. Org. Chem.* 1996, 61, 2326-2331. (b) Routier, S.; Cotelle, N.; Catteau, J. -P.; Bernier, J. -L.; Waring, M. J.; Riou, J. -F.; Bailly, C. *Bioorg. Med. Chem.* 1996, 4, 1185-1196) 4 (500 mg, 1.38 mmol) and Raney-Ni (1 g) were added to ammonia saturated MeOH (20 mL) and stirred under hydrogen gas (6.8 atm) at 50° C. After 72 hrs, this mixture was filtered. Solvent was removed under reduced pressure to yield the desired product (colorless oil, 360 mg, 72%). $^1$H NMR ($CDCl_3$) δ 1.4-1.6 (m, 16H), 1.78 (m, 2H), 2.70-3.10 (m, 4H), 4.8 (bs, 2H), 5.1 (bs, 2H), 7.31 (m, 5H). HRMS (FAB) Calcd (M+H$^+$) $C_{19}H_{32}N_3O_4$: 366.2393, found: 366.2401.

(S)-6-(tert-Butyloxycarbonyl)-1,2,6-triaminohexane (5). A solution of the triamine above (350 mg, 0.96 mmol) in MeOH (100 mL) was combined with Pd/C (10%, 40 mg) and stirred under hydrogen gas (1 atm) over night at room temperature. The mixture was filtered and evaporated under reduced pressure to yield a crude pink solid (180 mg, 82%) that was used below without purification. $^1$H NMR ($CDCl_3$) δ 1.40-1.60 (m, 15H), 1.88 (m, 2H), 2.70-3.10 (m, 4H), 4.80 (m, 4H). FAB m/z 232 (M+H$^+$).

(S)-N, N'-Bis(3-hydroxysalicylidene)-6-(tert-butyloxycarbonyl)-1,2,6-triaminohexane nickel complex (6). (Routier, S.; Bernier, J -L.; Waring, M. J.; Colson, P.; Houssier, C.; Bailly, C. *J. Org. Chem.* 1996, 61, 2326-2331. (b) Routier, S.; Cotelle, N.; Catteau, J. -P.; Bernier, J. -L.; Waring, M. J.; Riou, J. -F.; Bailly, C. *Bioorg. Med. Chem.* 1996, 4, 1185-1196) 2,4-Dihydroxybenzaldehyde (239 mg, 1.73 mmol) and 5 (200 mg, 0.866 mmol) were dissolved in dry EtOH (45 mL) and heated to reflux under $N_2$ for 30 min. Nickel acetate (861 mg, 3.46 mmol) was then added and heating was continued for 3 hours. During this period, the clear solution became orange. The solvent was evaporated under reduced pressure, and the remaining solid was subjected to silica chromatography using a solvent system of $CH_2Cl_2$/MeOH (10/1). The desired product 6 was isolated in 78% yield (357 mg). $^1$H NMR ($CD_3OD$) δ 1.26-1.52 (m, 13H), 1.80 (m, 2H), 2.97-3.04 (m, 3H), 3.15-3.16 (m, 1H), 3.63 (m, 1H), 6.09 (m, 2H), 6.23 (s, 2H), 7.00 (d, $J_1$=8.4 Hz, 1H), 7.05 (d, $J_2$=8.8 Hz, 1H), 7.44 (s, 1H), 7.47 (s, 1H). $^{13}$C NMR ($CD_3OD$) δ 24.2, 28.8, 30.8, 36.7, 41.1, 63.6, 69.4, 79.9, 105.4, 107.4, 107.5, 115.8, 116.1, 155.4, 135.7, 158.6, 162.1, 163.1, 164.5, 164.6, 166.7, 166.9. HRMS(FAB) Calcd (M+H$^+$) $C_{25}H_{32}N_3O_6Ni$: 528.1644, found: 528.1628.

(S)-N, N'-Bis(3-hydroxysalicylidene)-1,2,6-triaminohexane, TFA, nickel complex. (Routier, S.; Bernier, J -L.; Waring, M. J.; Colson, P.; Houssier, C.; Bailly, C. *J. Org. Chem.* 1996, 61, 2326-2331. Routier, S.; Cotelle, N.; Catteau, J. -P.; Bernier, J. -L.; Waring, M. J.; Riou, J. -F.; Bailly, C. *Bioorg. Med. Chem.* 1996, 4, 1185-1196.) TFA (75 μL) was added dropwise over 30 min to a solution of 6 (10 mg, 0.0189 mmol) in $CH_2Cl_2$ (2.0 mL) at room temperature under $N_2$. After stirring for an additional 30 min, the solvent was removed under reduced pressure. EtOH (5 mL) was twice added and evaporated to help remove residual TFA. The crude produce was dissolved in MeOH and precipitated by addition of $CH_2Cl_2$ to yield an orange solid (6.9 mg, 86%). $^1$H NMR ($CD_3OD$) δ 1.39 (m, 8H), 2.88 (m, 2H), 3.59

(m, 1H), 6.09 (m, 1H), 6.22 (s, 1H), 6.40 (d, J=8.2 Hz, 1H), 7.02 (m, 1H), 7.06 (m, 1H), 7.45 (m, 2H). $^{13}$C NMR (CD$_3$OD) δ 22.5, 26.7, 27.1, 35.1, 39.0, 62.2, 67.9, 103.9, 106.1, 106.2, 108.4, 114.3, 114.6, 134.0, 160.9, 161.8, 163.1, 165.5. HRMS (FAB) Calcd (M+H$^+$−TFA) C$_{20}$H$_{24}$N$_3$O$_4$Ni: 428.1120, found: 428.1161.

(S)-N, N'-Bis(3-hydroxysalicylidene)-6-biotinyl-1,2,6-triaminohexane nickel complex (7). A mixture of the Boc-deprotected TFA salt above (20 mg, 0.047 mmol), N-hydroxysuccinimide biotin ester (16 mg, 0.047 mmol) and triethylamine (8 μL) in dry DMF (4 mL) was stirred at 4' C. for 72 hours. Solvent was removed under reduced pressure, and the solid residue was subjected to silica gel chromatography using a solvent system of CH$_2$Cl$_2$/MeOH (5/1). The desired product 7 was isolated as an orange solid (6.4 mg, 22%). $^1$H NMR (CD$_3$OD) δ 1.26-1.57 (m, 12H), 2.11 (m, 2H), 2.66 (m, 1H), 2.88 (m, 1H), 3.01 (m, 1H), 3.18 (m, 3H), 3.60 (m, 2H), 4.30 (m, 1H), 4.48 (m, 1H), 6.11 (m, 2H), 6.24 (s, 2H), 7.07 (m, 2H), 7.49 (s, 1H), 7.51 (s, 1H). $^{13}$C NMR (CD$_3$OD) δ 24.2, 26.9, 29.4, 29.7, 30.2, 30.8, 36.6, 36.8, 40.0, 41.1, 57.1, 61.6, 63.4, 63.7, 69.3, 105.4, 107.5, 107.6, 115.8, 116.1, 135.4, 135.4, 135.7, 162.2, 163.2, 164.6, 166.7, 167.0, 176.1 HRMS (FAB) Calcd (M+H$^+$) C$_{30}$H$_{38}$N$_5$O$_6$Ni: 654.1896, found: 654.1866.

(S)-N, N'-Bis(3-(3-trimethylaminopropoxy)salicylidene)-6-biotinyl-1,2,6-triaminohexane nickel complex (2). 3-Bromopropyltrimethylammonium bromide (15.9 mg, 0.061 mmol) and K$_2$CO$_3$ (8.6 mg) were added to a solution of 7 (10 mg, 0.0153 mmol) in DMF (3 mL) and stirred at room temperature for three days (Kayser, L. A., M. S. thesis, University of Utah, 1997). The solvent was removed under reduced pressure to yield a crude solid. The solid was dissolved in water (1 mL) and a solution of KClO$_4$ (1 M) was slowly added dropwise until the first indication of precipitation was evident. This mixture was cooled to 4° C. overnight. The resulting precipitate was collected by filtration, redissolved in MeOH and precipitated with Et$_2$O. This procedure was repeated twice. The precipitate was isolated by filtration and recrystallized twice with MeOH/Ether. The desired product 2 was obtained as an orange solid (12.8 mg, 80%). $^1$H NMR (CD$_3$CN) δ 1.25-1.50 (m, 18H), 1.75 (m, 1H), 2.03 (m, 1H), 2.70 (m, 1H), 2.80 (m, 1H), 3.03 (bs, 18H), 3.11 (m, 4H), 3.40 (m, 2H), 3.56 (m, 1H), 4.04 (m, 2H), 4.23 (m, 1H), 4.38 (m, 1H), 4.95 (s, 1H), 5.35 (bs, 1H), 6.16-6.29 (m, 4H), 7.12 (m, 2H), 7.49 (s, 2H). $^{13}$C NMR (CD$_3$CN) d 23.77, 26,54, 28.89, 28.95, 29.76, 30.35, 36.05, 36.41, 39.26, 41.20, 54.01, 56.36, 60.70, 62.42, 63.40, 64.96, 65.16, 69.00, 103.14, 103.27, 106.44, 134,86, 135.18, 161.78, 162.78, 163.74, 164.23, 173.75. ESI-MS: m/z 954.4 ([M$^+$-ClO$_4$], 3%), 427.7 ([M$^+$−2(ClO$_4$)]/2, 100%).

Biotin-S-oxide. MMPP (49 mg, 0.10 mmol) was added to a solution of biotin (10 mg, 0.041 mmol) in 10 mM phosphate pH 7.0 (1 mL) and incubated at room temperature for 30 min. After removing the solvent under reduced pressure, crude product was dissolved in a solution of glacial acetic acid (20 μL) and absolute ethanol (1 mL) and maintained at 4° C. for 2 days. The crystalline product was filtered, washed and dried to yield 9.2 mg (85%). m.p. 239-242° C. ((Melville, D. B. J. Biol. Chem. 1954, 208, 495-500) 238-241° C.).

DNA experiments. The oligonucleotide 5'-d(AAAATATCAGATCTAAAA; SEQ ID NO: 1) was prepared by automated solid-phase synthesis, purified using a NAP™-25 column (Pharmacia Biotech) and 5' end-labeled with $^{32}$P using T4 kinase and gamma-[$^{32}$P]-ATP. DNA (11 μM, 6 nCi) was mixed with the Ni(salen)-biotin conjugate 2 (50 μM) in sodium phosphate (10 mM, pH 7.0) and incubated under ambient conditions for 10 min. Reaction was then initiated by addition of MMPP (120 μM) to a final volume of 50 μL. After further incubation for 30 min, a loading buffer (8 M urea) was added, and the samples were directly analyzed by denaturing polyacrylamide gel electrophoresis (20%) and phosphoimagery.

The DNA adduct formed by the Ni(salen)-biotin conjugate was isolated on a preparative scale using non-radiolabeled DNA. Reaction conditions were identical to those described above. Only the final reaction volume was increased to 2.5 mL. After incubation, this volume was reduced by 20% under vacuum and then applied directly to a monomeric avidin column (2 mL, Pierce). Unmodified DNA was eluted with a solution of 150 mM NaCl in 100 mM sodium phosphate pH 7.2. The DNA conjugate was eluted with 2 mM biotin in the solution above as described by the manufacturer. The salts and free biotin of the elution buffer were removed by reverse phase (C-18, Sep-Pak) chromatography using water and then 30% CH$_3$CN in water as solvents. The isolated conjugate was lyophilized, dissolved in ammonium acetate (10 M, 50 μL) and precipitated with ethanol/isopropanol prior to alternative radiolabeling and analysis by electrospray mass spectrometry. Strand fragmentation of the adduct was accomplished by resuspending a dried and radiolabeled sample in piperidine (0.2 M, 60 μL), heating to 90° C. for 30 min and finally lyophilizing. Residual piperidine was removed by repeated cycles of resuspending (water) and drying the solid pellet.

Example 3

Preparation of Salen-XaaHis Motif for Metal-Mediated Oxidative DNA-Peptide Cross-Linking Metallopeptide motifs of the N-terminal sequence XaaXaaHis, wherein histidine resides in the third position of the peptide, were first described for albumins (Harford, C.; Sarkar, B. Acc. Chem. Res. 1997, 30, 123-130.) and later utilized as redox-active bioconjugates for DNA cleavage (Mack, D. P.; Iverson, B. L.; Dervan, P. B. J. Am. Chem. Soc. 1988, 110, 7572-7574.) (Shullenberger, D. F.; Eason, P. D.; Long, E. C. J. Am. Chem. Soc. 1993, 115, 11038-11039.) (Nagaoka, M.; Hagihara, M.; Kuwahara, J.; Sugiura, Y. J. Am. Chem. Soc. 1994, 116, 4085-4086.) and protein-protein cross-linking. (Brown, K. C.; Yang, S. -H.; Kodadek, T. Biochemistry 1995, 34, 4733-4739.) Metallosalens are another class of tetradentate ligands that have seen applications to DNA chemistry. (Burrows, C. J.; Rokita, S. E. Acc. Chem. Res. 1994, 27, 295-301.) (Morrow, J. T.; Kolasa, K. A. Inorg. Chim. Acta 1992, 195, 245.) (Gravert, D. J.; Griffin, J. H. Inorg. Chem. 1996, 35, 4837-4847.) (Routier, S.; Bernier, J. -L.; Catteau, J. -P.; Bailly, C. Bioorg. Med. Chem. Lett. 1997, 7,63-66.) (Routier, S.; Bernier, J. -L.; Waring, M. J.; Colson, P.; Houssier, C.; Bailly, C. J. Org. Chem. 1996, 61, 2326-2331.) The juxtaposition of these two motifs leads to a Schiff-base metallopeptide hybrid that might combine the molecular recognition features of a peptide with the chemical reactivity of salicylaldimine complexes. Toward this end, we describe the synthesis and characterization of a prototypical member of this new "salen-XaaHis" ligand class and an example of DNA-peptide cross-linking.

Bidentate and tridentate Schiff-base adducts to peptides have been previously described, including complexes of a broad range of transition metals. (Sakurai, T.; Hongo, J. -I.; Nakahara, A. Inorg. Chim. Acta 1980, 46, 205-210.) (Col, B.

Figure 4:
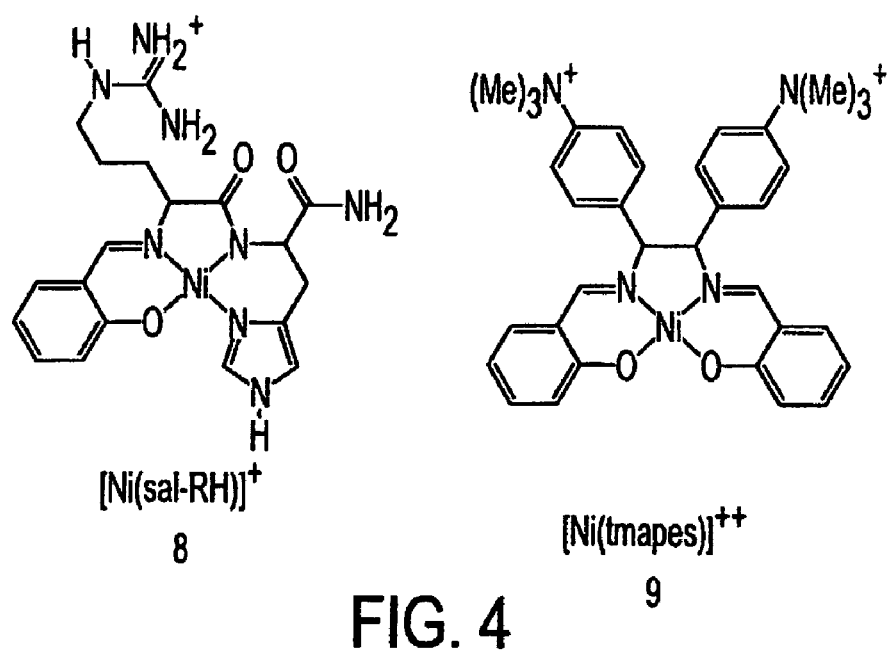
FIG. 4 shows the formula for (Ni(salen-ArgHis))⁺.

M.; Shimizu, K. D.; Krueger, C. A.; Harrity, J. P. A.; Snapper, M. L.; Hoveyda, A. H. *Angew. Chem. Int. Ed. Engl.* 1996, 35, 1668-1671.) These chelates have shown applications as diverse as asymmetric addition of CN⁻ to aldehydes, (Mori, A.; Nitta, H.; Kudo, M.; Inoue, S. *Tetrahedron Lett.* 1991, 32, 4333-4336.) epoxides (Shimizu, K. D.; Cole, B. M.; Krueger, C. A.; Kuntz, K. W.; Snapper, M. L.; Hoveyda, A. H. *Angew. Chem. Int. Ed. Engl.* 1997, 36, 1704-1707.) and imines. (Sigman, M. S.; Jacobsen, E. N. *J. Am. Chem. Soc.* 1988, 120, 4901-4902.) The majority of these complexes involve tridentate chelation via the phenolate oxygen, the imine nitrogen and the first amine bond of the peptide. By including a histidine residue in position 2 of the peptide, we now extend the coordination environment to a square-planar, tetradentate mode while still allowing for C-terminal elaboration of the peptide. See FIG. 4, compexes 8 and 9.

Figure 5:
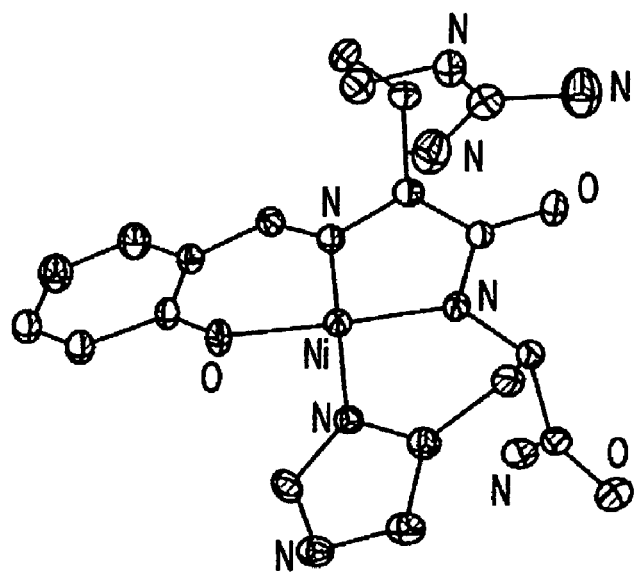
FIG. 5 shows an ORTEP plot of [Ni(salen-ArgHis)] $CH_3CO_2·3H_2O$, 8; the hydrogen atoms are omitted for clarity. Selected bond lengths (Å) and angles (deg): Ni—O (1), 1.8555(14); Ni—N(1), 1.8576(14); Ni—N(2), 1.8721 (15); Ni—N(3), 1.8931(14); N(1)—C(7), 1.285(3); N(1)—C(8), 1.484(2); N(2)—C(9), 1.337(2); N(2)—C(10), 1.459 (2); N(5)—C(15), 1.327(3); O(1)—Ni—N(1), 94.05(7); O(1)—Ni—N(2), 1.77.08(8); N(1)—Ni—N(2), 85.14(7); O(1)—Ni—N(3), 87.91(7); N(1)—Ni—N(3), 177.54(7); N(2)—Ni—N(3), 92.98(7).

Arginine (Arg) was chosen for position "Xaa" of the salen-XaaHis motif in order to impart water solubility and some degree of DNA affinity to the complex. [Ni(salen-ArgHis)]OAc, 8 (FIG. 4), was synthesized by addition of bis-(salicylaldehyde)Ni to a pH 8, 1:2 ethanol/water solution of the dipeptide, Arg-His bearing a C-terminal carboxamide. Orange microcrystals were obtained from this solution after 4 h at room temperature; crystals suitable for x-ray crystallographic analysis were obtained by recrystallization from 2:1 methanol/water. The crystal structure of 8, shown in FIG. 5, depicts the tetradentate nature of the salen-ArgHis ligand as predicted. (Crystal data (293 K) for [Ni(salen-ArgHis)]OAc·3H$_2$O, 8: NiC$_{21}$H$_{34}$N$_8$O$_8$, M$_r$=585.27, monoclinic, space group C2, a=17.0767(3), b=9.1342(3), c=16.3666(5) Å, α=90, β=101.4810(16), γ=90°, V=2501.81 (12) Å$^3$, Z=4, GOF=1.089. Final R values (t>2σI): R1=0.0334, wR2=0.0969.) The coordination geometry about the nickel ion is square planar as evidenced by the very small deviation (0.001 Å) from the plane defined by the four ligand donor atoms. The overall charge on the molecule is positive due to the guanidino moiety of arginine; an acetate counter ion is present in a hydrogen-bonded network of 3 water molecules associated with the periphery of the ligand.

Consistent with the crystal structure, the solution structure of [Ni(salen-ArgHis)]⁺ appears to be that of a square-planar, diamagnetic species based on the NMR and uv-visible absorption spectra (d-d transition at 398 nm, e=1,930 cm⁻¹M⁻¹). Cyclic voltammetric studies of 8 (FIG. 4) as a 1 mM aqueous solution (pH 7, 10 mM NaP$_i$, 100 mM NaCl) showed a largely irreversible oxidation at E$_p$~+0.85 V vs. Ag/AgCl (scan rate=100 mV s⁻¹), although some evidence for a small reduction at 0.80 V could be detected (i$_{pc}$/i$_{pa}$~0.4). This behavior is consistent with ligand-centered oxidation due to the facile formation of a phenolate radical, as is typically observed in Ni(salen) complexes.

The ligand-centered redox chemistry of the new Ni(salen-XaaHis) complex immediately suggested that it might participate in an oxidative cross-link with DNA. We previously reported that the water-soluble salen complex, Ni(TMAPES), 9, formed an adduct to guanine residues under oxidative conditions. (Burrows, C. J.; Rokita, S. E. *Acc. Chem. Res.* 1994, 27, 295-301.) (Muller, J. G.; Paikoff, S. J.; Rokita, S. E.; Burrows, C. J. *J. Inorg. Biochem.* 1994, 54, 199-206.) (Burrows, C. J.; Muller, J. G. *Chem. Rev.* 1998, 98, 1109-1151.) In those studies, treatment of DNA or RNA with 9 in the presence of KHSO$_5$ led to the formation of a guanine adduct that could be characterized by electrospray ionization MS (ESI-MS), (Muller, J. G.; Kayser, L. A.; Paikoff, S. J.; Duarte, V.; Tang, N.; Rokita, S. E.; Burrows, C. J. *Coord. Chem. Rev.* 1999, 185-186, 761-774) primer extension assays, (Woodson, S. A.; Muller, J. G.; Burrows, C. J.; Rokita, S. E. *Nucleic Acids Res.* 1993, 21, 5524-5525.) and PAGE analysis of short oligonucleotides. (Muller, J. G.; Paikoff, S. J.; Rokita, S. E.; Burrows, C. J. *J. Inorg. Biochem.* 1994, 54, 199-206.) The participation of the phenolate moiety in 9 as part of the cross-link was confirmed through substituent effect studies, (Muller, J. G.; Kayser, L. A.; Paikoff, S. J.; Duarte, V.; Tang, N.; Rokita, S. E.; Burrows, C. J. *Coord. Chem. Rev.* 1999, 185-186, 761-774) and the modified guanine was found to be a piperidine-labile DNA cleavage site (Muller, J. G.; Paikoff, S. J.; Rokita, S. E.; Burrows, C. J. *J. Inorg. Biochem.* 1994, 54, 199-206.) (Muller, J. G.; Kayser, L. A.; Paikoff, S. J.; Duarte, V.; Tang, N.; Rokita, S. E.; Burrows, C. J. *Coord. Chem. Rev.* 1999, 185-186, 761-774.).

Figure 6:
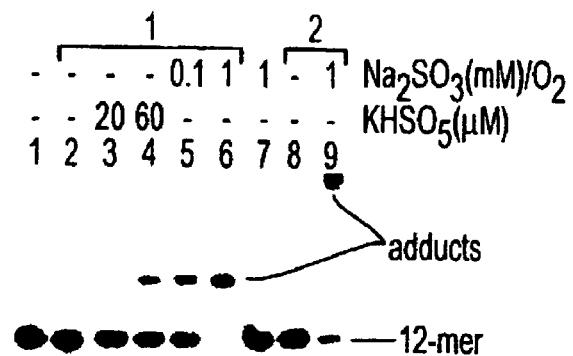
FIG. 6 shows phosphorimage of 20% polyacrylamide denaturing gel (7 M urea) showing high-molecular weight adducts to DNA formed with nickel complexes. The 12-mer oligodeoxynucleotide, 5'-d(ATATCAGATCTA; SEQ ID NO: 2)-3', was labeled at the 5' terminus with $^{32}$P and incubated with reactants under the standard conditions described in Supporting Information. Lane 1: DNA alone. Lane 2: control with 100 μM Ni(salen-ArgHis) only. Lanes 3-6: 100 μM 8 plus the indicated concentrations of oxidant. Lane 7: control showing the effect of $Na_2SO_3$ without metal complex. Lane 8: control with 2 μM 9. Lane 9: 2 μM 9 plus $Na_2SO_3$. All experiments were carried out in the presence of air and included EDTA in the workup. Cross-linking yields in lanes 3, 4, 5, and 6 were 16, 36, 39, and 80%, respectively.

Studies reported herein show that the cross-linking behavior of a phenolate moiety can now be incorporated into the N-terminal motif of a peptide. As shown in FIG. 6, treatment of a 5'-[$^{32}$P]-end-labeled 12-mer oligodeoxynucleotide with 8 (100 μM) and KHSO$_5$ (20 or 60 μM, lane 3 or 4), followed by quenching with HEPES+EDTA, led to a high molecular weight band observable by PAGE. Interestingly, 8 appears to share with nickel peptides (Muller, J. G.; Hickerson, R. P.; Perez, R. J.; Burrows, C. J. *J. Am. Chem. Soc.* 1997, 119, 1501-1506.) and nickel salens the ability to catalyze HSO$_5$- formation in situ via autoxidation of sulfite. Thus, cross-linking of 8 to DNA was even more effective when KHSO$_5$ was replaced with Na$_2$SO$_3$ (0.1 or 1 mM, lane 5 or 6). Sulfite can be used in greater concentration than HSO$_5$⁻, an oxidant that would lead to indiscriminant background oxidation of DNA if used in concentration >100 μM. Control studies confirmed that no high molecular weight band was observed if Ni²⁺+ArgHis (lacking salicylaldehyde) was used in place of 8. The position on the gel of the high molecular-weight bands from 8 are significantly lower than that from 9 (whose DNA cross-link is shown for comparison in FIG. 6, lane 9), suggesting that the charge and molecular weight of this adduct are different. It is noted that 8 was used in higher concentration than 9 because of its lower electrostatic attraction for DNA. Extension of the peptide to include a DNA-binding moeity should greatly reduce the required concentration of metal complex.

Figure 7:
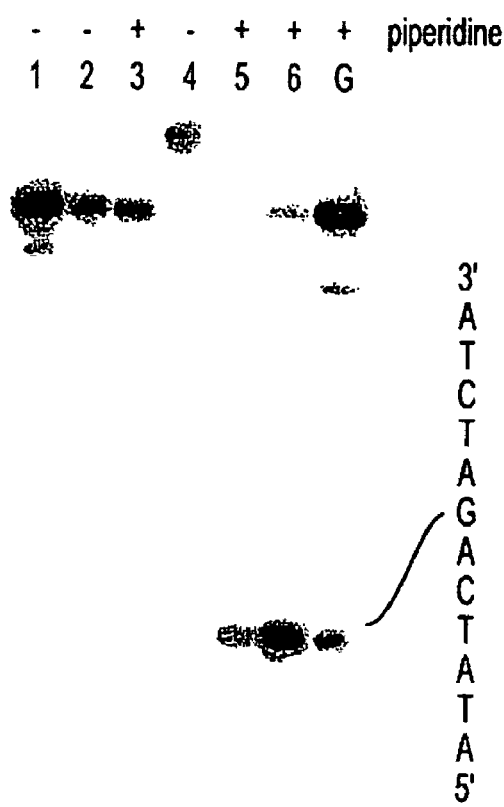
FIG. 7 shows the effect of piperidine treatment of the DNA-Ni(salen-ArgHis) adduct. Reactions were run in a similar manner as those in FIG. 6. Lane 1: control using 100 μM $Ni(OAc)_2$, 100 μM ArgHis dipeptide and 1 mM $Na_2SO_3$, showing that a high-molecular-weight species does not form in the absence of salicylaldehyde. Lanes 2—6: Reactions with 100 μM 1 and 1 mM $Na_2SO_3$ followed by piperidine treatment (0.2 M, 90° C., 30 min) when so indicated. Lanes 2 and 3: 12-mer oligonucleotide (SEQ ID NO: 2) band cut and isolated from a previous gel after the adduct had formed. Lanes 4 and 5: Band corresponding to high-molecular-weight adduct cut and isolated from a previous gel. Lane 6: Typical reaction of 100 μM 1, 1 mM $Na_2SO_3$ with piperidine treatment. Lane G: Maxam-Gilbert G lane using dimethylsulfate.

Treatment of the [Ni(salen-ArgHis)]⁺-modified DNA with 0.2 M piperidine at 90° C. for 30 min. led to substantial cleavage, but only at the single G residue of the oligomer (see FIG. 7). Several other oligonucleotide sequences were used, and all gave the same G chemistry as described here. Control studies demonstrated that no other base modifications, such as imidazolone formation, (Cadet, J.; Berger, M.; Buchko, G. W.; Joshi, P. C.; Raoul, S.; Ravanat, J. -L. *J. Am. Chem. Soc.* 1994, 116, 7403-7404.) were produced by these reaction conditions. The piperidine sensitivity of the DNA adduct suggests that the cross-link has likely formed to either N7 or C8 of G, since both of these sites of modification typically lead to piperidine-induced strand scission. (Burrows, C. J.; Muller, J. G. *Chem. Rev.* 1998, 98, 1109-1151.) Indeed, arylation of guanine at both of these positions has been observed for the phenolic A-ring of estrogen. (Akanni, S.; Tabakovic, K.; Abul-Hajj, Y. J. *Chem. Res. Toxicol.* 1997, 10, 477-481.) Mass spectral analysis provided further information on the site and identity of adduct formation; isolation of the major 8·DNA adduct from the gel and precipitation with NH$_4$OAc led to a sample suitable for ESI-MS. The final spectrum showed a single product of mass 3739 consistent with DNA+salicylaldehyde−10 Daltons (see FIG. 8). The overall loss of 10 mass units corresponds to the now generally observed phenomenon of further oxidation of any C8-modified guanine adduct leading to a guanidinohydantoin product after hydration and decarboxylation of C6 of the purine. (Duarte, V.; Muller, J. G.; Burrows, C. J. *Nucleic Acids Res.* 1999, 27, 496-502.) (Poje, M.; Sokolic-Maravic, L. *Tetrahedron* 1988, 44, 6723-6728.) (Shibutani, S.; Gentles, R. G.; Iden, C. R.; Johnson, F. *J. Am.*

*Chem. Soc.* 1990, 112, 5667-5668.) Thus, the DNA partner in cross-link formation appears to be C8 of G, and the imine bond was hydrolyzed to leave a salicylaldehyde end product due to the EDTA quench. A higher, faint band visible in lane 6 of FIG. 6 was also analyzed by ESI-MS and found to correspond to the intact nickel complex 8 adducted to the guanidinohydantoin moiety of the DNA strand (i.e. DNA+ 8−10=4089 Daltons). This band is more pronounced if EDTA is omitted from the quenching step. On the salen-ArgHis ligand, the positions ortho and para to the phenol oxygen are suspected sites of reactivity based on inhibition of cross-linking when these sites are substituted in 9 (Muller, J. G.; Kayser, L. A.; Paikoff, S. J.; Duarte, V.; Tang, N.; Tang, N.; Rokita, S. E.; Burrows, C. J. *Coord. Chem. Rev.* 1999, 185-186, 761-774.) Final confirmation of the structure of the adduct awaits large-scale preparation and x-ray or NMR characterization.

In summary, the new hybrid ligand salen-XaaHis, as demonstrated in the prototype complex 8 (from FIG. 4), combines the chemical reactivity of a salen complex with the potential molecular recognition properties of a peptide. In principle, any protein or peptide containing histidine as the second residue (and not containing proline as the N-terminal residue) may now be converted to a DNA or RNA cross-linking agent. After hydrolysis of the imine linkage, one obtains a nucleic acid specifically derivatized with a salicylaldehyde moiety at the cross-link site. This unique aldehyde might be further conjugated to fluorescent or biotinylated probes for analysis of peptide/protein binding sites in DNA or RNA.

Example 4

Synthesis and characterization of (Ni(salen-ArgHis) OAc, 8: 30.2 mg (0.17 mmol) of bis-(salicylaldehyde)nickel(II) (synthesized in a 1:2 combination of Ni(OAc)$_2$ and salicylaldehyde) was added to 200 µL of aqueous 0.5 M argininylhistidine carboxamide (purchased from BACHEM). The volume was adjusted to 20 mL with a 2:1 water:ethanol solution. The mixture was adjusted to pH 8 with 1 N KOH in EtOH and stirred at 25° C. for 4 h. The undissolved, green, bis-(salicylaldehyde)nickel(II) was filtered from the solution. Orange microcrystals precipitated from the filtrate after cooling and were washed with small amounts of CHCl$_3$ to remove any remaining salicylaldehyde. A 40% yield (35.5 mg, 0.067 mmol) of product was realized. X-ray quality crystals were obtained by redissolving the orange microcrystals in 2:1 methanol:water and show evaporation of solvent to form red needles. High resolution FAB-MS(positive ion) in CH$_3$OH gave m/z=471.14 (M+H$^+$), Calcd m/z=471.14. $^1$H NMR (d$_6$-DMSO): δ 1.68 (m, 2H, Arg-H$_\gamma$), 1.86 (s, 3H, acetate), 1.92 (m, 2H, Arg-H$_\beta$), 3.10 (d, 2H, His-H$_\beta$), 31.5 (m, 2H, Arg-H$_A$) 3.86 (m, 2H, His-H$_\alpha$ and Arg-H$_\alpha$), 6.53 (t, 1H, salen-H$_4$ or H$_5$), 6.78 (d, 1H, salen H$_6$), 6.97 (s, 1H, His-H$_4$), 7.16 (t, 1H, salen-H$_4$ or H$_5$), 7.29 (d, 1H, salen-H$_3$), 7.71 (s, 1H, His-H$_2$), 7.89 (s, 1H, imine). $^{13}$C NMR(d$_6$-DMSO, ppm) 23.33, 28.47, (Arg-C$_{\beta+\gamma}$) 32.05 (His-C$_\beta$), 40.72 (Arg-C$_\delta$), 50.17 (His-C$_\alpha$), 68.80 (Arg-C$_\alpha$), 114.17, 114.58, 120.43, 120.65, (salen-C$_3$, C$_6$ and C$_1$, His-C$_2$), 132.89, 132.97, 133.40, 134.93, (salen-C$_4$ and C$_5$, His-C and C$_4$) 156.60 (Guanidino), 161.54, 162.84, 173.98, 178.01 (imine, salen-C$_2$, and 2 amide C=O). IR bands at 1675, 1620, 1589, 1476, 1389, 1204, 834, 801, 721 and 625 cm$^{-1}$. UV-vis: 322 nm (ε=3860), shoulder at 342 nm (ε=2990), 398 nm (□=1930 cm$^{-1}$M$^{-1}$).

DNA experiments: The oligonucleotide was purchased from Oligos, etc. and purified by FPLC (pH 12, anion exchange). The DNA was 5' end-labeled with $^-$P using T4 kinase and (γ-$^{32}$P)-ATP. Each reaction contained 3 µM (10 nCi) of oligodeoxynucleotide, 3 µM calf thymus DNA (per base pair), 10 mM NaP$_i$ (pH 7.0) and 100 mM NaCL with a total volume of 50 µL. The nickel complex was added in aliquots of 10 µL and allowed to incubate with the DNA for 10 min. Then, a 2-µL aliquot of the specified oxidant was added and the samples were left open to the air since O$_2$ is necessary to activate sulfite. After 1 hour, the samples were quenched with 2 µL of 250 mM EDTA (pH=8) and individually dialyzed with water (3×12 hrs.). Piperidine treatment involved the addition of 60 µL of 0.2 M piperidine to the dried samples and incubation for 30 min. at 90° C.

Figure 8:
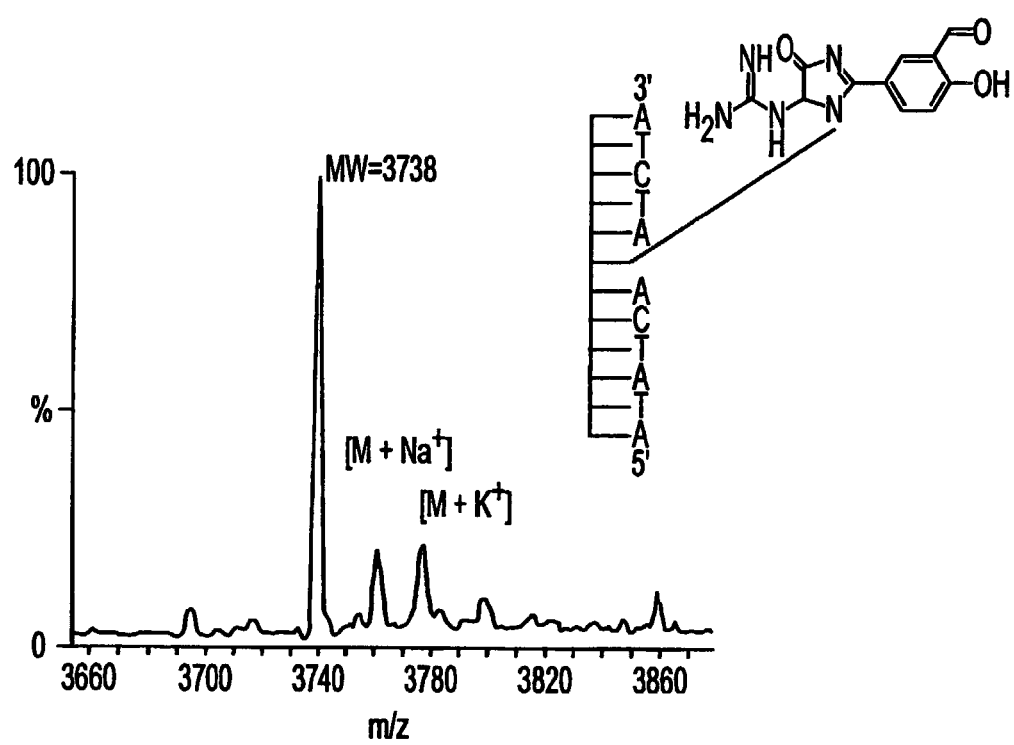
FIG. 8 shows ESI-MS spectrum of the high molecular weight adduct isolated from the reaction of the 12-mer oligodeoxynucleotide (SEQ ID NO: 2) and Ni(salen-ArgHis) with sulfite and $O_2$. The molecular weight of the 12-mer itself is 3628 as determined by ESI-MS. (R. J. Perse, Ph.D., Dissertation, University of Utah, 1997) The proposed structure of the salicylaldehyde adduct is shown.
Figure 9:
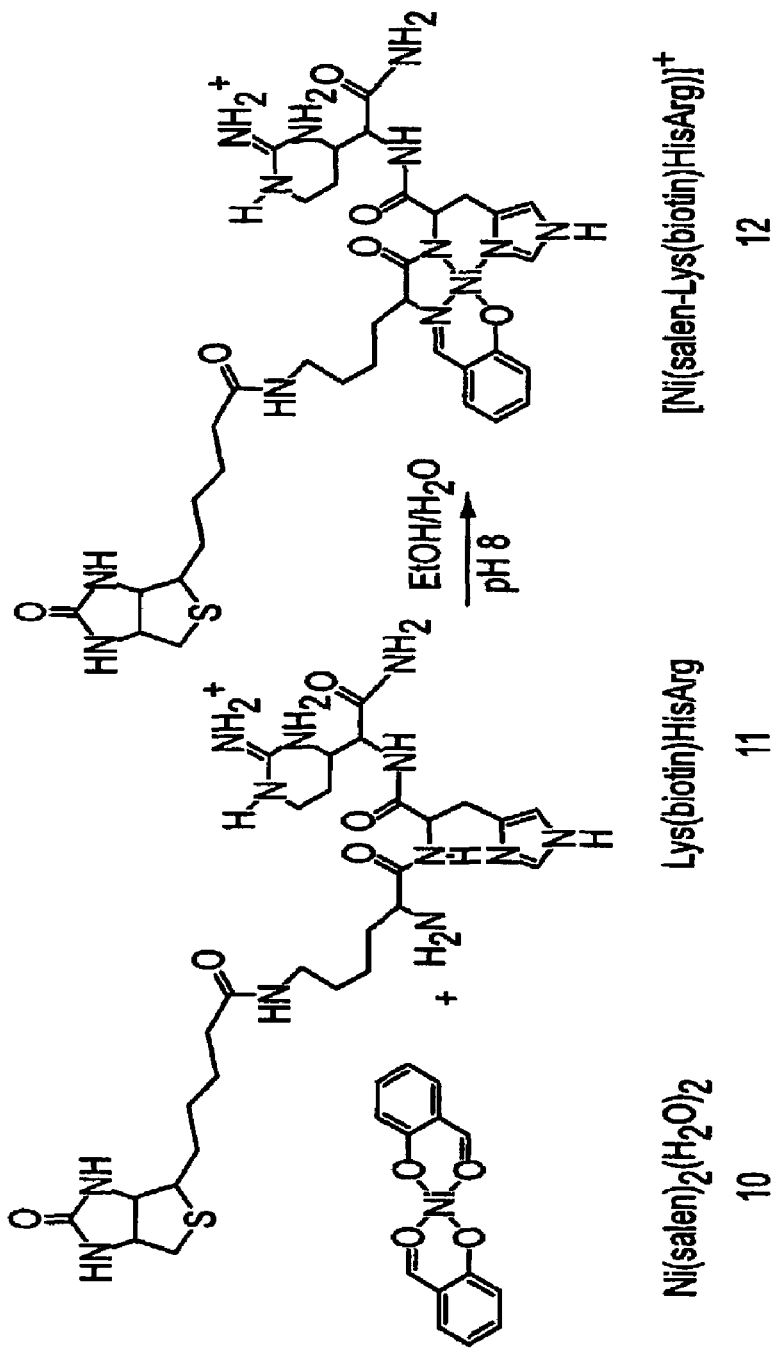
FIG. 9 shows a schematic for synthesizing Ni(salen-Lys (biotin)HisArg) 12.

The ESI-MS samples were prepared by isolating the high molecular weight adduct on a gel and then precipitating the DNA with ethanol/isopropanol. Forty Eppendorf tubes of the reaction of 8 with DNA and sulfite were prepared. Each reaction mixture contained, 20 µM of the oligodeoxynucleotide, 200 µM of Ni(salen-ArgHis), 100 mM NaCl/10 mM NaP$_i$, and 1 mM sulfite in a final 100 µL reaction volume. The reactions were left open to the air and quenched with 10 mM EDTA after 2½ hours. The samples were dialyzed with a 1000 dalton molecular weight cut-off membrane against water for 2 days. The reacted material was separated from starting material by gel electrophoresis using a 20% polyacrylamide denaturing gel. The bands were visualized by placing the gel on a silica plate shining UV light on it. The band corresponding to the high molecular weight adduct was cut out and deposited in a microcentrifuge tube filters (Spin-X, 0.22 µM cellulose acetate) with 300 µL of water. After agitating the tubes for several hours the samples were centrifuged to separate the sample from the gel and then dialyzed against water for 2 days. The samples were dialyzed for one more day against 10 mM ammonium acetate. The samples were combined into 2 tubes and freeze dried. The samples were dissolved in 30 µL of 10 M ammonium acetate and 30 µL of water. Then, the high molecular weight adduct was precipitated with ethanol/isopropanol. After 30 µL of water was added, 0.36 OD of product was obtained. This sample was freeze dried then dissolved in 50 µL of a 1:1 solution of 1 mM HN$_4$OAc(pH 7) and isopropanol for injection into the mass spectrometer (FIG. 8).

Example 5

Experimental Details of (Ni(Salen-Lys(Biotin)HisArg) 12 Synthesis

The tripeptide ligand was synthesized using a general solid phase peptide synthesis protocol. The peptide was synthesized on a Rink Amide AM resin, which after cleavage of the peptide, leaves a carboxamide C-terminus. In the first coupling to the resin, Fmoc-Arg(pbf)-OH was added. An endcapping step was added using acetic anhydride. The N-terminus was deprotected with a 50% piperidine solution in DMF. Then Fmoc-His(trt)-OH was coupled to the growing peptide chain. After the subsequent endcapping and deprotection steps, Dde-Lys(fmoc)-OH was added. The fmoc group on the α amino group was removed with piperidine and then coupled to D(+)-Biotin. The coupling steps were activated by coupling reagents N-methylmorpholine and HBTU in DMF. The Dde protecting group on the N-terminus of Lys(biotin)HisArg 11 was removed with 2% hydrazine in DMF. The peptide chain was cleaved from the resin using a cleavage cocktail of 95% TFA and 0.5% TIS. The cleavage cocktail was reacted with the resin beads for three hours using a wrist-action shaker. The cleaved peptide solution was collected and dried. The residue was washed with ether and dried. The peptide was purified by HPLC using a gradient of 0.1% TFA aqueous solution with a 60% acetonitrile/40% of aqueous 0.1% TFA solution. The peak with a retention time of 9 min was collected. ESI-MS confirmed that this peak contained the tripeptide. An NMR spectra showed that the sample was pure. The metal complex of the peptide ligand was prepared by Schiff base formation at the N-terminus and deprotonation of the amide. An aqueous 4 mM solution of Lys(biotin)HisArg 11 was adjusted to pH=8 using 0.1 N KOH (in ethanol). To this solution was added an excess of Ni(salicyladehyde)$_2$(H$_2$O)$_2$ 10 an insoluble green compound. The solution was stirred for 3 hours then filtered through a cellulose acetate filter to remove any unreacted Ni(salicylaldehyde)$_2$(H$_2$O)$_2$ 10. The solution was washed twice with an equal volume of chloroform to remove any excess salicylaldehyde. This orange solution of [Ni(salen-Lys(biotin)HisArg)]$^+$ 12 was shown to have the characteristic uv/vis spectrum of square planar nickel complexed to a schiff base ligand.

The protected amino acids and resin was purchased from Novasyn (Calbiochem). The Biotin was purchased from ACROS. All solvents were reagent grade.

All of the references cited herein are incorporated by reference in their entirety.

wherein:

B independently represents doubly bonded oxygen;

C represents carbon;

D independently represents nitrogen or oxygen;

L is a detectable label, optionally attached to a linker;

M represents a nickel ion;

b is from 0 to 6;

n is 0 to 1;

R' represents hydrogen, alkyl, aryl or a peptide chain;

R" is R, R' or G;

G represents OH, an amide or a DNA delivery agent; and

R represents a nitrogen-containing cationic group, optionally attached to a linker, wherein said cationic group is at least one $C_b$ group linked to a nitrogen atom, $(CH_2)_3$ $NH_2$, $(CH_2)_2$ $NH_2$, $C_bN$ $(C_b)_{0-3}$,

---

---

What is claimed is:

1. A labeled nickel complex compound having formula I:

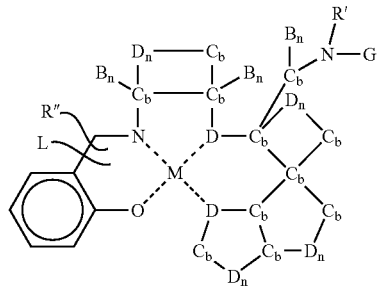

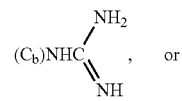

pyridyl.

2. The labeled nickel complex compound of claim 1, wherein said DNA delivery agent comprises intercalators, oligonucleotides, proteins or polyamines.

3. The labeled nickel complex compound of claim 1, wherein R' is a peptide chain.

4. The labeled nickel complex of claim 1, wherein the detectable label is a radioactive compound, a protein ligand, a fluorescent compound or an enzyme.

5. The labeled nickel complex compound of claim 1, wherein the detectable label is biotin.

6. A labeled nickel complex compound, having formula A or B:

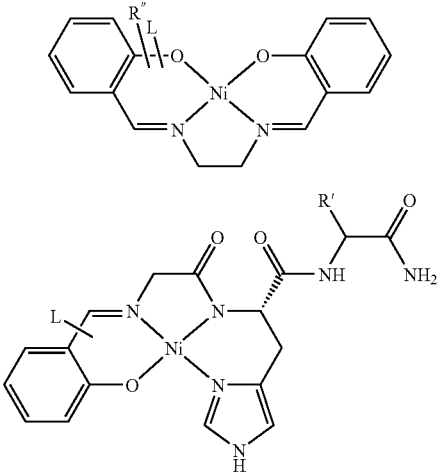

wherein:
R' represents hydrogen, alkyl, aryl or a peptide chain;
R" represents R, R' or G;
L is a detectable label, optionally attached to a linker;
G represents —OH, —OR, an amide or a DNA delivery agent; and
R represents a nitrogen-containing cationic group optionally attached to a 1 nker, wherein said cationic group is at least one $C_b$ group linked to a nitrogen atom, $(CH_2)_3$ $NH_2$, $(CH_2)_4$ $NH_2$, $C_bN$ $(C_6)_{0-3}$,

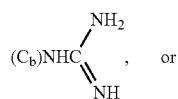

pyridyl
and wherein the label is biotin.

7. A labeled nickel complex compound, which is Ni-salen-biotin complex.

8. A labeled nickel complex compound, which is Ni(salen-Lys(biotin) His Arg) complex.

9. A method for detecting a non-canonical nucleic acid sequence comprising binding the labeled nickel complex compound of claim 1, to a sample of nucleic acid, and detecting a signal of the detectable label on the labeled nickel complex compound.

10. A method for detecting a non-canonical nucleic acid sequence comprising binding the labeled nickel complex compound of claim 6, to a sample of nucleic acid, and detecting a signal of the detectable label on the labeled nickel complex compound.

11. A labeled hybrid compound comprising the labeled nickel complex compound of claim 1, complexed with a protein or oligonucleotide.

12. The labeled hybrid compound of claim 11, wherein the labeled nickel complex compound is labeled with a radioactive compound, a protein ligand, a fluorescent compound or an enzyme.

13. A labeled hybrid compound comprising the labeled nickel complex compound of claim 6, complexed with a protein or oligonucleotide.

14. The labeled hybrid compound of claim 13, which is complexed with the protein; wherein a penultimate amino acid from the N-terminus of the protein is histidine.

15. A method for detecting or measuring protein-nucleic acid interaction comprising mixing the labeled hybrid compound of claim 11, with a solution of nucleic acid, and assaying for the signal from a detectable label attached to the nucleic acid.

16. A method for purifying a nucleic acid-nickel-complex adduct, comprising:
   a) mixing the labeled nickel complex compound of claim 1, with a solution of DNA,
   b) subjecting the mixture of step a) to a separation medium, wherein the medium contains a material that specifically binds to the label, and
   c) separating the bound medium from the solution mixture, wherein the adduct is bound to the material of the separation medium.

17. The method of claim 16, wherein said separation medium is affinity chromatography.

18. The method of claim 17, wherein said label is biotin, and the material in the separation medium binds to biotin.

19. The method of claim 18, wherein the material binding to biotin is avidin.

20. The method of claim 18, wherein the material binding to biotin is streptavidin.

21. A method for purifying a nucleic acid-nickel-complex adduct, comprising:
   a) mixing the labeled nickel complex compound of claim 6, with a solution of DNA,
   b) subjecting the mixture to a separation medium, wherein the medium contains a material that specifically binds to the label, and
   c) separating the bound medium from the solution mixture, wherein the adduct is bound to the material of the separation medium.

22. The method of claim 21, wherein said separation medium is affinity chromatography.

23. The method of claim 21, wherein the material binding to biotin is avidin.

24. The method of claim 21, wherein the material binding to biotin is streptavidin.

25. A method for detecting or measuring protein-nucleic acid interaction comprising mixing the labeled hybrid compound of claim 6, with a solution of nucleic acid, and assaying for the signal from a detectable label attached to the nucleic acid.

* * * * *